(12) United States Patent
Anderson et al.

(10) Patent No.: US 11,992,675 B2
(45) Date of Patent: May 28, 2024

(54) IMPLANTABLE MEDICAL DEVICE INCLUDING A TINE HOUSING

(71) Applicant: Medtronic, Inc., Minneapolis, MN (US)

(72) Inventors: Thomas A. Anderson, New Hope, MN (US); Douglas D. Nippoldt, Centerville, MN (US); Benjamin Cook, Woodbury, MN (US); Carlos Taboada, St-Prex (CH)

(73) Assignee: Medtronic, Inc., Minneapolis, MN (US)

( * ) Notice: Subject to any disclaimer, the term of this patent is extended or adjusted under 35 U.S.C. 154(b) by 187 days.

(21) Appl. No.: 17/109,865

(22) Filed: Dec. 2, 2020

(65) Prior Publication Data

US 2021/0236814 A1 Aug. 5, 2021

Related U.S. Application Data

(60) Provisional application No. 62/970,049, filed on Feb. 4, 2020.

(51) Int. Cl.
*A61N 1/05* (2006.01)
*A61N 1/375* (2006.01)

(52) U.S. Cl.
CPC ....... *A61N 1/0573* (2013.01); *A61N 1/37518* (2017.08); *A61N 1/3754* (2013.01)

(58) Field of Classification Search
CPC .............. A61N 1/0573; A61N 1/37518; A61N 1/3754; A61N 1/3756
See application file for complete search history.

(56) References Cited

U.S. PATENT DOCUMENTS

| | | |
|---|---|---|
| 3,814,104 A | 6/1974 | Irnich et al. |
| 3,943,936 A | 3/1976 | Rasor et al. |
| 4,041,956 A * | 8/1977 | Purdy ................ A61N 1/37512 607/36 |
| 4,103,690 A | 8/1978 | Harris |
| 4,142,530 A | 3/1979 | Wittkampf |
| 4,269,198 A | 5/1981 | Stokes |

(Continued)

FOREIGN PATENT DOCUMENTS

| | | |
|---|---|---|
| WO | 2002022202 A2 | 3/2002 |
| WO | 2006118865 A2 | 11/2006 |

OTHER PUBLICATIONS

International Search Report and Written Opinion of International Application No. PCT/US2021/013848, dated May 4, 2021, 11 pp.

(Continued)

*Primary Examiner* — Allen Porter
*Assistant Examiner* — Adreanne A. Arnold
(74) *Attorney, Agent, or Firm* — Shumaker & Sieffert, P.A.

(57) ABSTRACT

An implantable medical device (IMD) including an elongated housing and a tine housing configured to attach to the elongated housing. The tine housing may support an extending plurality of tines and a distal-most electrode. An inner chamber is bounded at least in part by the elongated housing and the tine housing with an adhesive fill port in fluid communication with the inner chamber. A method of assembling the IMD includes forming the inner chamber and substantially filling the inner chamber with an adhesive through the adhesive fill port. The method may include curing the filling adhesive.

20 Claims, 10 Drawing Sheets

(56) References Cited

U.S. PATENT DOCUMENTS

| | | |
|---|---|---|
| 4,280,512 A | 7/1981 | Karr et al. |
| 4,858,623 A | 8/1989 | Bradshaw et al. |
| 4,936,823 A | 6/1990 | Colvin |
| 5,193,540 A | 3/1993 | Schulman et al. |
| 5,411,535 A | 5/1995 | Fujii et al. |
| 5,573,540 A | 11/1996 | Yoon |
| 5,683,447 A | 11/1997 | Bush et al. |
| 6,007,558 A | 12/1999 | Ravenscroft et al. |
| 6,151,525 A | 11/2000 | Soykan et al. |
| 6,240,322 B1 | 5/2001 | Peterfeso et al. |
| 6,286,512 B1 | 9/2001 | Loeb et al. |
| 6,409,674 B1 | 6/2002 | Brockway et al. |
| 6,575,967 B1 | 6/2003 | Leveen et al. |
| 6,783,499 B2 | 8/2004 | Schwartz |
| 6,915,149 B2 | 7/2005 | Ben-Haim |
| 6,978,178 B2 | 12/2005 | Sommer et al. |
| 7,290,743 B2 | 11/2007 | Nowack |
| 7,418,298 B2 | 8/2008 | Shiroff et al. |
| 8,353,940 B2 | 1/2013 | Benderev |
| 9,351,648 B2 * | 5/2016 | Mothilal .............. A61B 5/349 |
| 10,052,127 B2 | 8/2018 | Wood |
| 10,099,050 B2 | 10/2018 | Chen et al. |
| 2002/0103424 A1 | 8/2002 | Swoyer et al. |
| 2002/0165589 A1 | 11/2002 | Imran et al. |
| 2003/0088301 A1 | 5/2003 | King |
| 2004/0147973 A1 | 7/2004 | Hauser |
| 2004/0230281 A1 | 11/2004 | Heil et al. |
| 2006/0084965 A1 | 4/2006 | Young |
| 2006/0085039 A1 | 4/2006 | Hastings et al. |
| 2006/0085041 A1 | 4/2006 | Hastings et al. |
| 2008/0183235 A1 * | 7/2008 | Stancer ............... A61N 1/375 |
| | | 607/36 |
| 2009/0082828 A1 | 3/2009 | Ostroff |
| 2012/0172690 A1 * | 7/2012 | Anderson ........... A61N 1/0573 |
| | | 607/18 |
| 2012/0172892 A1 | 7/2012 | Grubac et al. |
| 2014/0039591 A1 | 2/2014 | Drasler et al. |
| 2015/0039070 A1 | 2/2015 | Kuhn et al. |
| 2016/0310723 A1 * | 10/2016 | Eggen ................ A61N 1/3756 |
| 2019/0083779 A1 * | 3/2019 | Yang .................. A61N 1/3752 |

OTHER PUBLICATIONS

Haqqani et al., "The Implantable Cardioverter-Defibrillator Lead: Principles, Progress and Promises," PACE, vol. 32, Oct. 2009, pp. 1336-1353.

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the EMPOWER leadless pacemaker and the EMBLEM subcutaneous ICD," Herzschrittmachertherapie + Elektrophysiologie, vol. 29, Oct. 31, 2018, pp. 355-361.

U.S. Appl. No. 62/970,049, filed Feb. 4, 2020, by Anderson et al.

* cited by examiner

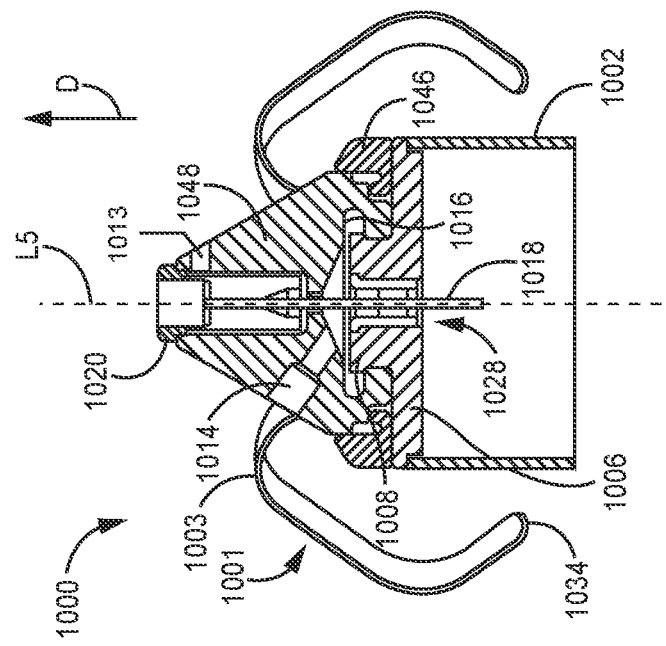
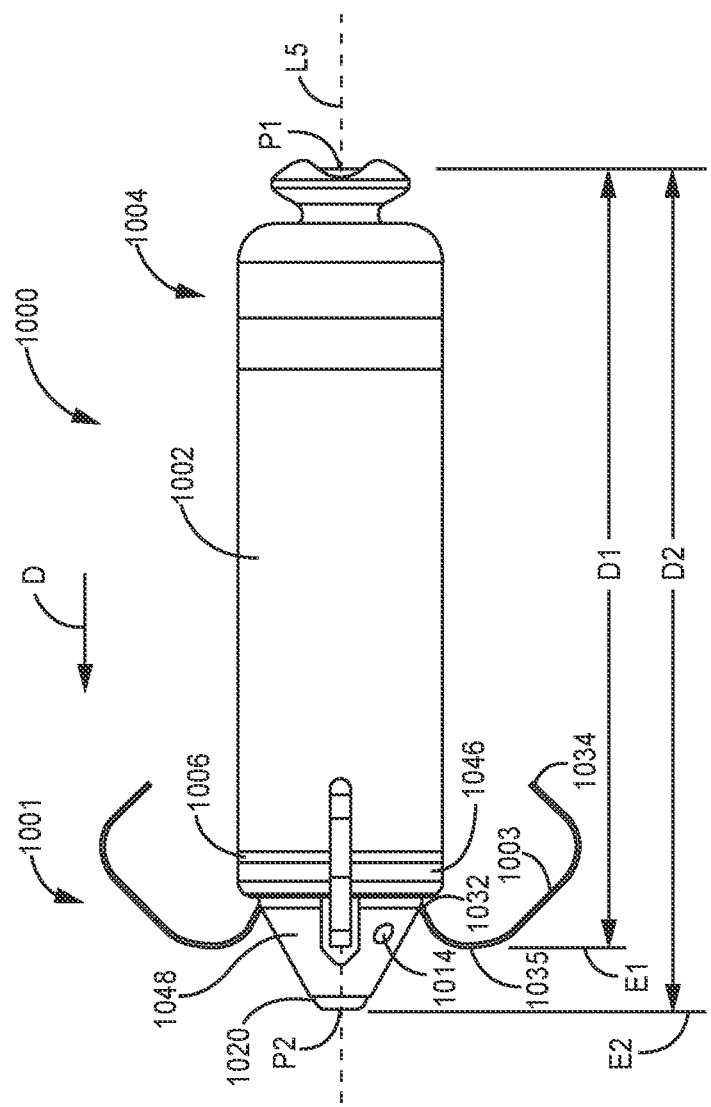

IMPLANTABLE MEDICAL DEVICE INCLUDING A TINE HOUSING

This application claims the benefit of U.S. Provisional Patent Application Ser. No. 62/970,049 (filed Feb. 4, 2020), which is entitled, "IMPLANTABLE MEDICAL DEVICE INCLUDING A TINE HOUSING," and incorporated by reference herein in its entirety.

TECHNICAL FIELD

This disclosure is related to medical devices such as relatively compact implantable medical devices.

BACKGROUND

Various types of implantable medical devices (IMDs) have been implanted for treating or monitoring one or more conditions of a patient. Such IMDs may be adapted to monitor or treat conditions or functions relating to heart, muscle, nerve, brain, stomach, endocrine organs or other organs and their related functions. Such IMDs may be associated with leads that position electrodes at a desired location or may be leadless with electrodes integrated with and/or attached to the device housing.

A cardiac pacemaker is an IMD configured to deliver cardiac pacing therapy to restore a more normal heart rhythm. Such IMDs sense the electrical activity of the heart, and deliver cardiac pacing based on the sensed electrical activity, via electrodes. Some cardiac pacemakers are implanted a distance from the heart and coupled to one or more leads that intravascularly extend into the heart to position electrodes with respect to cardiac tissue. Some cardiac pacemakers are sized to be completely implanted within one of the chambers of the heart, and may include electrodes integrated with or attached to the device housing rather than leads.

SUMMARY

The disclosure provides implantable medical devices (IMD) comprising an elongated housing and tine housing. The tine housing is configured to attach to a distal end of the elongated housing to form an inner chamber, where the inner chamber is bounded at least by some portion of the tine housing and the elongated housing. The tine housing includes an adhesive fill port in fluid communication with the formed inner chamber. An adhesive may be directed through the adhesive fill port to substantially fill the inner chamber and form a contiguous mass of adhesive in contact with the tine housing and the distal end of the elongated housing. The cured adhesive may provide fastening between the tine housing and the distal end of the elongated housing. A feedthrough pin establishing electrical connection to a distal-most electrode may extend through the inner chamber formed, such that the cured adhesive lends lateral and radial support to the feedthrough pin. The cured adhesive may also contribute to electrical isolation between the feedthrough pin and other components of the IMD, and may provide fluid protection and/or isolation to some portion of or all of a hermetic feedthrough assembly, feedthrough section, or an interior portion of an elongated housing of the IMD.

The tine housing may be configured to receive one or more locking tabs of a mounting structure attached or integrally formed with the elongated housing. The tine housing may be configured to receive the one or more locking tabs in a manner whereby the tine housing is substantially secured against movement relative to the elongated housing and parallel to a longitudinal axis of the IMD. The tine housing may include an upper tine housing and a lower tine housing, where the upper tine housing receives the one or more locking tabs and limits motion of the lower housing relative to at least the distal end of the elongated housing. A plurality of tines attached to the tine housing may extend distally from the tine housing and radially away from the longitudinal axis of the IMD. The plurality of tines may be trapped between the upper tine housing and the lower tine housing when the upper tine housing receives the one or more locking tabs of the mounting structure.

In an example, a medical device comprises an elongated housing defining a longitudinal axis, wherein the longitudinal axis extends from a proximal end of the elongated housing to a distal end of the elongated housing. A mounting structure is attached to the distal end of the elongated housing, wherein the mounting structure comprises one or more locking tabs around the longitudinal axis. A tine housing at least partially surrounding the mounting structure, with the tine housing comprising an adhesive fill port, and with the tine housing configured to receive the one or more locking tabs. The one or more locking tabs trap the tine housing to substantially prevent motion of the tine housing parallel to the longitudinal axis. The tine housing and the mounting structure form an inner chamber bounded at least in part by the distal end of the elongated housing, the mounting structure, and the tine housing when the tine housing receives the one or more locking tabs, and the adhesive fill port is in fluid communication with the inner chamber when the tine housing receives the one or more locking tabs.

In an example, a technique for assembling a medical device comprises attaching a tine housing of the medical device to an elongated housing of the medical device, wherein the elongated housing defines a longitudinal axis that extends from a proximal end of the elongated housing to a distal end of the elongated housing. Attaching the tine housing to the elongated housing comprises receiving, by the tine housing, at least one locking tab of a mounting structure attached to the distal end of the elongated housing, wherein the at least one locking tab is configured to substantially prevent motion of the tine housing parallel to the longitudinal axis when the tine housing receives the one or more locking tab. The technique includes filling an inner chamber of a medical device with an adhesive using an adhesive fill port defined by the tine housing, wherein the tine housing and the mounting structure form the inner chamber bounded at least in part by the distal end of the elongated housing, the mounting structure, and the tine housing when the tine housing receives the one or more locking tabs, and wherein the adhesive fill port is in fluid communication with the inner chamber when the tine housing receives the one or more locking tabs.

The details of one or more examples are set forth in the accompanying drawings and the description below. Other features, objects, and advantages will be apparent from the description and drawings, and from the claims.

BRIEF DESCRIPTION OF DRAWINGS

FIG. 10 is an elevation view illustrating an additional example IMD including a tine housing and elongated housing.

FIG. 11 is a schematic cross-sectional view of the example IMD of FIG. 10.

DETAILED DESCRIPTION

Figure 1:
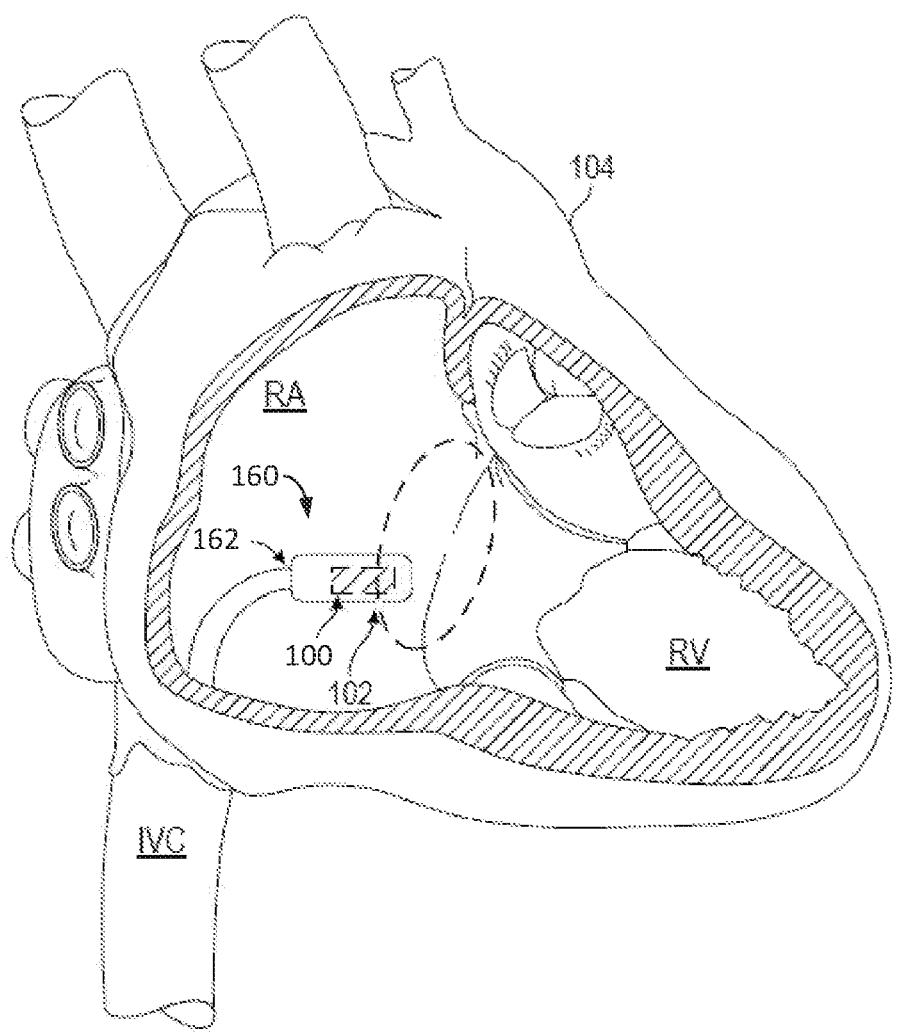
FIG. 1 is a conceptual diagram illustrating an example IMD implanted at an example target implant site.

This disclosure describes implantable medical devices (IMDs) that includes an elongated housing and a tine housing, with the tine housing mated to a distal end of the elongated housing with a mounting structure. One or more locking tabs of the mounting structure insert into the tine housing, trapping the tine housing to substantially prevent longitudinal movement of the tine housing relative to the elongated housing. When mated, the tine housing, the mounting structure, and the distal end of the elongated housing generally form an inner chamber in the distal portion of the IMD. The inner chamber is a volume generally encompassed within the tine housing and bordered by the distal end of the elongated housing. An adhesive fill port typically in the tine housing is in fluid communication with the inner chamber formed. A feedthrough pin configured to electrically communicate with an electrode extends from a distal portion of the tine housing, through the inner chamber, and into the elongated housing of the IMD.

The inner chamber may be filled with an adhesive administered through the adhesive fill port. The tine housing may further include a vent port in fluid communication with the inner chamber, in order to promote complete filling of the inner chamber with the adhesive. The configuration of the IMD allows the adhesive to form a contiguous mass within the inner chamber which contacts an interior of the tine housing, the distal end of the elongated housing, and the mounting structure, as well as some portion of the feedthrough pin extending through the inner chamber. Solidification of the contiguous mass of adhesive thus provides secure attachment of the tine housing and feedthrough pin to the elongated housing. Further, the solidified adhesive may increase the radial support of the feedthrough pin as it extends from a distal portion of the tine housing, through the inner chamber, and into the elongated housing of the IMD. The cured adhesive may also contribute to electrical isolation between the feedthrough pin and other components of the IMD, and may provide fluid protection and/or isolation to some portion of or all of a hermetic feedthrough assembly, feedthrough section, or an interior portion of an elongated housing of the IMD.

The locking tabs of the mounting structure may be arranged around a longitudinal axis of the elongated housing of the IMD ("IMD longitudinal axis"). A locking tab may comprise a flange extending in a direction substantially perpendicular to the IMD longitudinal axis (e.g., extending in a generally radial direction relative to the IMD longitudinal axis). The one or more locking tabs may insert into the tine housing via recesses having a longitudinal portion oriented substantially in a direction parallel to the IMD longitudinal axis. The receiving receptor recesses within the tine housing may have an additional locking portion which extends in a direction substantially perpendicular to the IMD longitudinal axis, such that the longitudinal portion and the locking portion together have a generally L-shaped cross-section. Once a locking tab is received within the longitudinal portion of the receptor recess, the tine housing may be rotated around the IMD longitudinal axis to place the locking tab within the locking portion of the receptor recess, substantially trapping (e.g., substantially limiting) the tine housing against movement in a direction parallel to the IMD longitudinal axis. Additionally, the longitudinal portion of a receptor recess may define a portion of the inner chamber formed when the one or more tabs trap the tine housing.

The tine housing of the IMD may include an upper tine housing and a lower tine housing. The upper tine housing may be configured to receive the one or more locking tabs of the mounting structure, and may be configured to trap the lower tine housing against the distal end of the elongated housing when the one or more locking tabs are received. In an example, when the upper tine housing traps the lower tine housing against the distal end of the elongated housing, the upper tine housing limits movement of the lower tine housing relative to the distal end of the elongated housing. The lower tine housing and the upper tine housing may be configured to substantially mate when the locking tabs trap the upper tine housing, such that the lower tine housing is between the upper tine housing and the distal end of the elongated housing of the IMD. For example, the lower tine housing or the upper tine housing may define a protrusion, and the other of the lower tine housing or the upper tine housing may define a recess configured to receive the protrusion when the one or more locking tabs trap the upper tine housing. The lower tine housing may include an annular component configured to at least partially surround the mounting structure and the IMD longitudinal axis when in contact with the distal end of the elongated housing, and may comprise an inner bearing shelf around some portion of the interior surface of the annulus. The upper tine housing may contact all or some portion of the inner bearing shelf when the one or more locking tabs trap the upper tine housing against motion parallel to the IMD longitudinal axis. In an example, when the upper tine housing is mated with the lower tine housing, the upper tine housing separates the lower tine housing and the inner chamber.

A plurality of tines may extend from the tine housing. The plurality of tines may be configured to extend outwardly from the tine housing in a substantially symmetric manner around the IMD longitudinal axis. A shape of each respective tine of the plurality of tines may be selected to control deployment, tissue fixation, and/or tissue disengagement. A tine may include a fixed end and a free end, with the fixed end supported by the tine housing. A first segment may extend from the fixed end and a second segment may extend from the first segment to the free end. The first segment and the second segment may be joined by an angular section. Further, the plurality of tines may be configured to assume one or more configurations. For example, the plurality of tines may assume a relaxed configuration where each free end of a tine is proximal to the angular section of the tine. The plurality of tines may also assume an extended configuration (for example, when sheathed within a delivery catheter) where each free end of a tine is distal to the angular section and the fixed end of the tine. In some examples, one or more fixed ends of the plurality of tines is attached to a tine ring, and the tine housing is configured to trap the tine ring. For example, the tine housing may trap the tine ring between an upper tine housing and a lower tine housing. In some examples, the tine housing may provide a snap-fit with the tine ring. In examples, when the tine housing traps the tine ring, the tine housing substantially limits movement of the tine ring relative to the tine housing (e.g., the upper tine housing and/or lower tine housing).

FIG. 1 is a conceptual diagram illustrating a portion of an example medical device system 160 configured to implant a relatively compact implantable medical device 100 ("IMD 100") at a target implant site 102. In some examples, as illustrated in FIG. 1, the target implant site 102 may include an appendage of a right atrium (RA) of the heart 104 of a patient. In some examples, target implant site 102 may include other portions of heart 104 or other locations within a body of the patient. Medical device system 160 may include a delivery tool 162 configured to house and controllably deploy relatively compact IMD 100. In some examples, a clinician may maneuver medical device system 160 to target implant site 102. For example, with the IMD loaded therein, the clinician may guide delivery tool 162 up through the inferior vena cava (IVC) and into the RA. In some examples, other pathways or techniques may be used to guide delivery tool 162 into other target implant sites within the body of the patient. Additionally, although FIG. 1 schematically illustrates an IMD configured as a cardiac pacemaker being delivered to a target site in a heart of a patient, the present disclosure is not limited solely to such IMD devices. The example systems, devices, and techniques described herein may find useful application a wide variety of IMDs.

Figure 2:
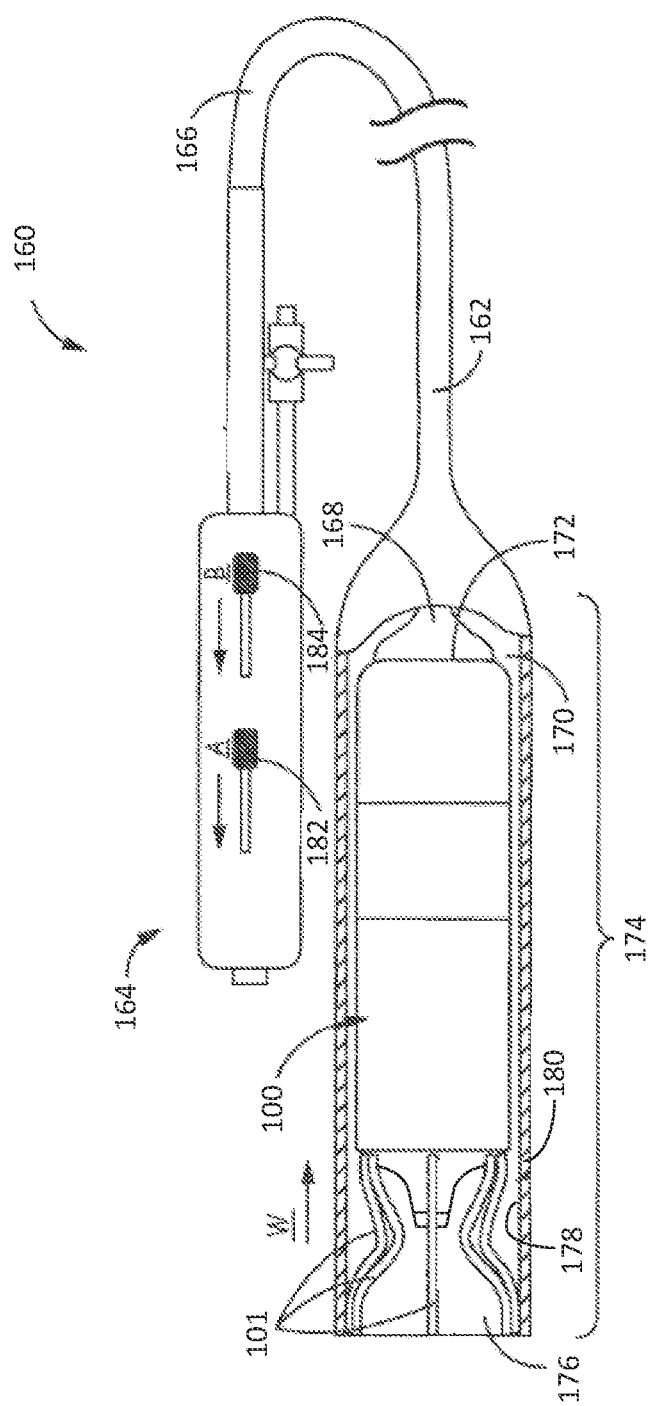
FIG. 2 is a schematic illustration of an example delivery device for an example IMD.

FIG. 2 is a conceptual diagram illustrating a partial cut-away section of the example medical device system 160 including a delivery tool 162 and IMD 100. For purposes of illustration, the distal portion of delivery tool 162 is enlarged relative to handle 164. During use, IMD 100 is loaded into delivery tool 162 for deployment to a target implant site (e.g. target implant site 102). Delivery tool 162 includes the handle 164, an elongate outer member 166, and an elongate inner member 168 that extends within lumen 170 of outer member 166. Inner member 168 includes a distal end 172, which is configured to engage IMD 100 by abutting a proximal end of IMD 100. An entirety of IMD 100 may be loaded within tubular sidewall 174 that defines a distal portion of outer member lumen 170, for example, having been loaded therein by pulling IMD 100, with the proximal end of IMD 100 leading, in through lumen distal opening 176. In some examples, an inner surface 178 of tubular sidewall 180 engages tines 101 of IMD 100 as IMD 100 is loaded into lumen 170. Inner sidewall 180 may to act to hold tines 101 in an extended configuration, as will be discussed.

Handle 164 may be configured to control movement of delivery tool 162 and/or deployment of IMD 100. The clinician may position medical device system 160 by advancing delivery tool 162 through vasculature of the patient, for example, from a femoral venous access site and up through the IVC, or a radial artery access site. Delivery tool 162 may include articulating features to facilitate the navigation of the distal portion of delivery tool 162. For example, inner member 168 may include a pull wire assembly (not shown) integrated therein and being coupled to control member 182 of handle 164 that, when moved per arrow A, causes inner member 168 and outer member 166 to bend along distal portions thereof.

In some examples, a proximal end of outer member 166 may be coupled to a control member 184 of handle 164 such that an entirety of outer member 166 is movable with respect to inner member 168, via control member 184. For example, after positioning medical device system 160 at selected tissue in proximity to a target implant site 102 (FIG. 1), a clinician may retract outer member 166, per arrow W, relative to IMD 100 and inner member 168 and deploy IMD 100 out through distal opening 176. Suitable construction detail for a delivery tool like delivery tool 162 is described in U.S. Pat. No. 10,052,127 to Wood et al., which is incorporated herein by reference in its entirety.

Figure 3:
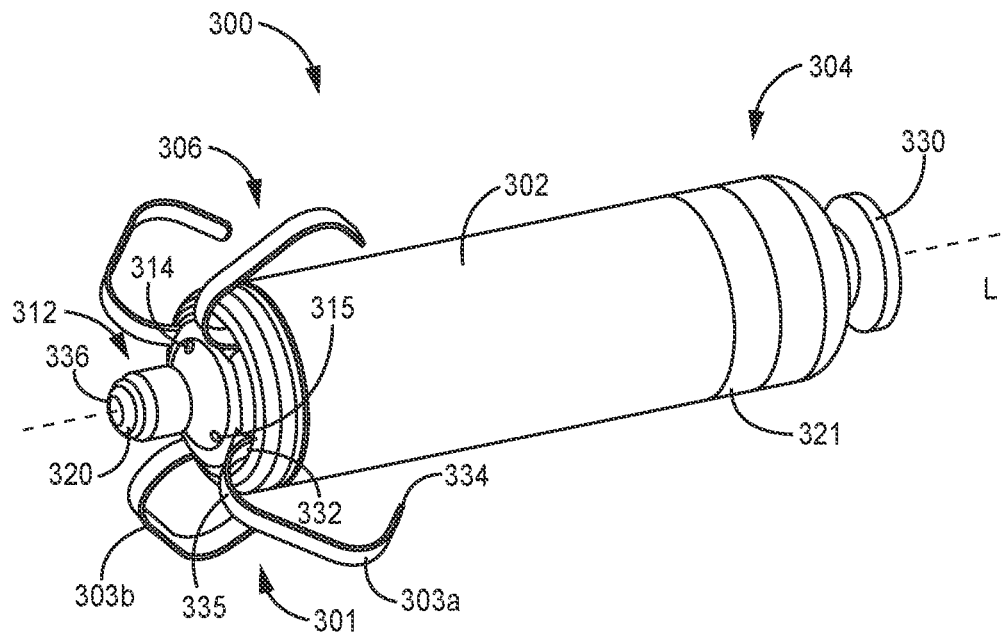
FIG. 3 is a perspective view illustrating an example IMD including a tine housing and elongated housing.
Figure 4:
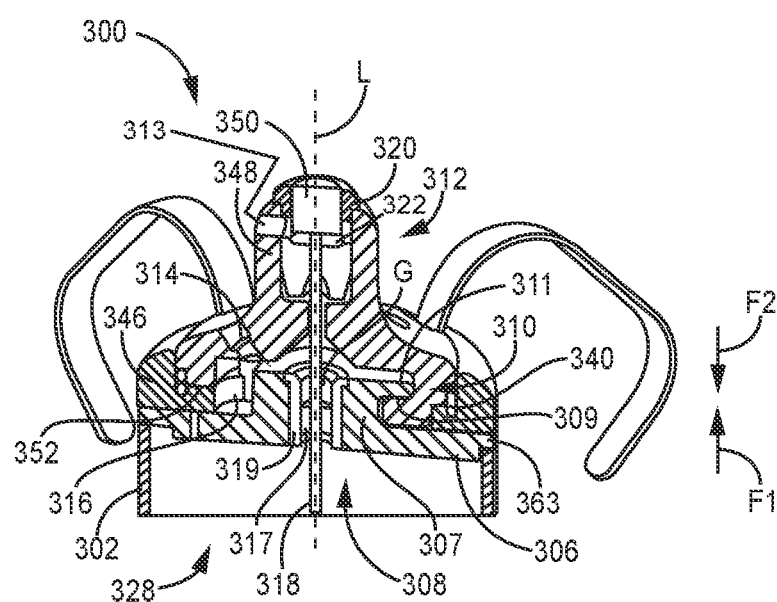
FIG. 4 is a schematic cross-sectional view of the example IMD of FIG. 3.

FIG. 3 is a conceptual diagram illustrating a plan view of a relatively compact IMD 300. IMD 300 may be an example of IMD 100 (FIGS. 1, 2). FIG. 4 illustrates a cross-section of a portion of IMD 300, where a cutting plane is taken perpendicular to IMD longitudinal axis L. IMD 300 comprises an elongated housing 302, with an IMD longitudinal axis L extending from a proximal end 304 of elongated housing 302 ("elongated housing proximal end 304") to a distal end 306 of elongated housing 302 ("elongated housing distal end 306"). Elongated housing 302 may be formed from a biocompatible and biostable metal such as titanium and may be overlaid with an insulative layer such as medical grade polyurethane, parylene, or silicone. In some examples, elongated housing 302 may enclose a hermetically sealed volume. IMD 300 may include any suitable dimensions. In some examples, an outer diameter of IMD 300 (e.g., outer diameter of elongated housing 302) may be between about 10 French (Fr) and about 30 Fr, such as about 20 Fr.

IMD 300 includes an electrode 320 supported in part by a tine housing 312 and generally surrounded by a plurality of tines 301, including tine 303a and tine 303b. A tine may be any elongate structure that extends from tine housing 312 to engage tissue and thereby fix IMD 300 at a target implant location. The plurality of tines 301 extends from a tine housing 312 at elongated housing distal end 306. IMD 300 may also include monolithic controlled release device (MCRD) 350. The plurality of tines 301 may be configured to hold or stabilize electrode 320 in intimate tissue contact at a target implant site, for example, within right atrium RA or within right ventricle RV (FIG. 1). IMD 300 may include a second electrode 321, which may be formed by removing a portion of the insulative layer to expose a metallic surface of elongated housing 302. Second electrode 321 may function in conjunction with electrode 320 for bipolar pacing and sensing. IMD 300 may contain electronic circuitry, including one or more of sensing circuitry (e.g., for sensing cardiac signals), therapy delivery circuitry (e.g., for generating cardiac pacing pulses), and processing circuitry for controlling the functionality of IMD 300, and may include a feedthrough pin 318 (FIG. 4) in electrical connection with electrode 320. The electronic circuitry may be configured to generate and deliver an electrical pulse therapy to tissue proximate electrode 320, through the tissue to second electrode 321. In some examples, IMD 300 includes a retrieval structure 330 fixedly attached to proximal end 304 of elongated housing 302 and configured for temporarily tethering IMD 300 to a delivery system such as delivery tool 162.

IMD 300 is configured to provide an arrangement whereby a solidified adhesive in a formed inner chamber 316 may be effectively utilized as a fastening method to provide stability of tine housing 312 relative to elongated housing distal end 306 (FIG. 4). Tine housing 312 is configured to secure to elongated housing distal end 306 in a manner which substantially precludes movement of tine housing 312 relative to elongated housing distal end 306 in a direction parallel to longitudinal axis L. Tine housing 312 and elongated housing distal end 306 are further configured such that, when tine housing 312 secures to elongated housing distal end 306, the inner chamber 316 is formed and bounded at least by some portion of tine housing 312 and elongated housing distal end 306. With tine housing 312 secured to elongated housing distal end 306, an adhesive may be administered through adhesive fill port 314 to form a contiguous mass of adhesive within inner chamber 316 and in contact with some portion of tine housing 312 and elongated housing distal end 306. In examples, the contiguous mass of adhesive is further in contact with some portion of mounting structure 308. The contiguous mass of adhesive may also be in contact with the feedthrough pin 318 as it passes through inner chamber 316. Curing of the contiguous mass of adhesive affixes tine housing 312 to elongated housing distal end 306 (and vice-versa), and may provide additional support to feedthrough pin 318 as it extends through inner chamber 316. When the contiguous mass is cured, a surface of tine housing 312, a surface of elongated housing distal end 306, or a surface of mounting structure 308 may be an adherends with any other of the surface of tine housing 312, the surface of elongated housing distal end 306, or the surface of mounting structure 308. A vent port 315 may also in fluid communication with inner chamber 316, to allow venting of inner chamber 316 during the adhesive fill.

Tine housing 312 secures to elongated housing distal end 306 via a mounting structure 308. Tine housing 312 may comprise a lower tine housing 346 mated with an upper tine housing 348, as will be discussed. Mounting structure 308 is attached to elongated housing distal end 306, and includes one or more locking tabs such as locking tab 310 positioned around the IMD longitudinal axis L. Tine housing 312 is configured to receive locking tab 310 in a manner whereby mounting structure 308 traps tine housing 312 to substantially prevent movement of tine housing 312 (relative to elongated housing 302) in a direction parallel to longitudinal axis L. When tine housing 312 is trapped, tine housing 312, mounting structure 308, and elongated housing distal end 306 form the inner chamber 316. An adhesive fill port 314 extends through tine housing 312 and is in fluid communication with inner chamber 316. An adhesive may be directed through adhesive fill port 314 to form a contiguous mass within inner chamber 316. The contiguous mass may contact the portions of tine housing 312, mounting structure 308, and elongated housing distal end 306 bounding inner chamber 316, such that upon solidification, the adhesive acts to secure tine housing 312 to mounting structure 308 and elongated housing distal end 306. A feedthrough pin 318 may additionally pass through inner chamber 316 and through the contiguous mass of adhesive. Elongated housing distal end 306 may be integrally formed with the remainder of elongated housing 302, or may comprise a distal end cap 363 secured to the remainder of elongated housing 302. Distal end cap 363 may be secured to the remainder of elongated housing 302 by welding, soldering, riveting, thread engagement, a snap-fit, adhesives, or some other fixation method.

Mounting structure 308 may include a base section 307 surrounding IMD longitudinal axis L and extending in a distal direction from elongated housing distal end 306. Locking tab 310 may extend from base section 307 in a direction substantially perpendicular to IMD longitudinal axis L. Locking tab 310 may include an overhang comprising a first tab surface 309 and a second tab surface 311, where the first tab surface 309 faces the elongated housing distal end 306 and the second tab surface 311 faces opposite the first tab surface 309. First tab surface 309 and/or second tab surface 311 may be substantially perpendicular to IDM longitudinal axis L. First tab surface 309 is configured to provide a reaction force against an object—such as some portion of tine housing 312—when the object applies an action force on first tab surface 309 in a direction from elongated housing proximal end 304 toward elongated housing distal end 306 (FIG. 3). For example, when some portion of tine housing 312 bears on and applies an action force in the direction F1 on first tab surface 309, first tab surface 309 is configured to provide a reaction force on the portion of tine housing 312 in the direction F2. In this manner, when tine housing 312 receives locking tab 310 and establishes a configuration where some portion of tine housing bears on first tab surface 309, locking tab 310 may substantially secure tine housing 312 against movement relative to elongated housing 302 and in a direction parallel to IMD longitudinal axis L.

Figure 5A:
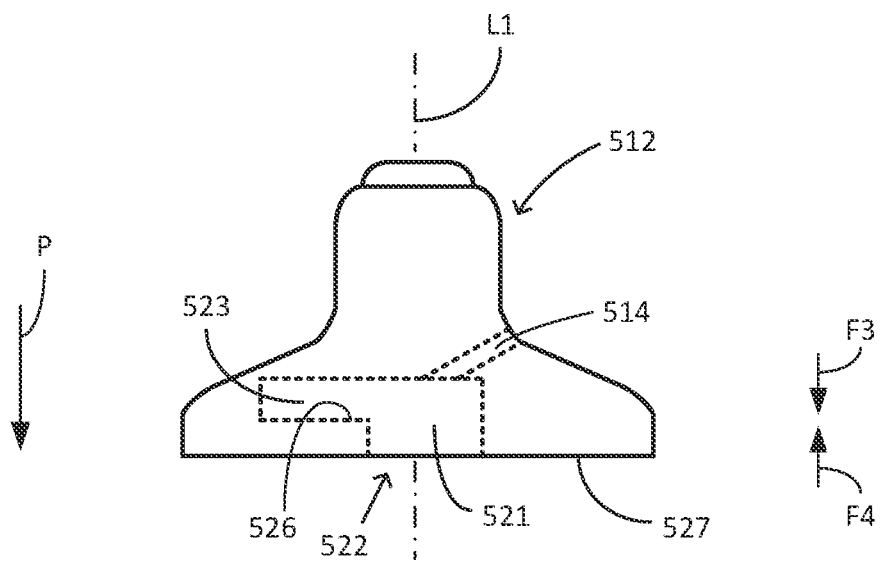
FIG. 5A is a front elevation view illustrating an example tine housing.
Figure 5B:
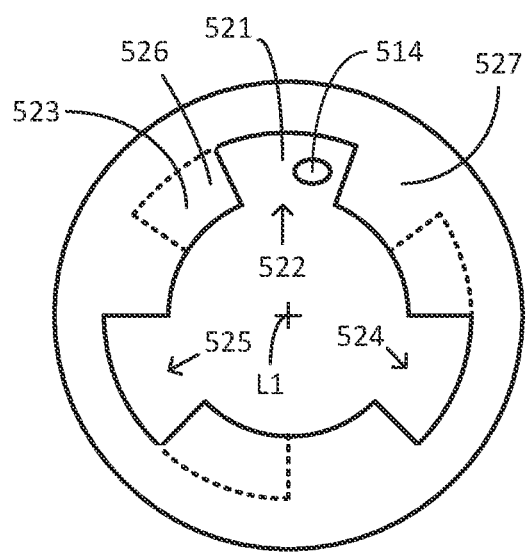
FIG. 5B is a bottom elevation view illustrating the example tine housing of FIG. 5A.

Tine housing 312 at least partially surrounds mounting structure 308 and IMD longitudinal axis L when tine housing 312 receives locking tab 310. Locking tab 310 and other locking tabs of mounting structure 308 may insert into tine housing 312 via respective receptor recesses. A receptor recess may have a longitudinal portion oriented substantially in a direction parallel to the IMD longitudinal axis. The receptor recess may have an additional locking portion which extends in a direction substantially perpendicular to the IMD longitudinal axis, such that the longitudinal portion and the locking portion together have a generally L-shaped cross-section. For example, FIG. 5A and FIG. 5B schematically illustrate a portion of a tine housing 512, with FIG. 5A providing a front elevation view and FIG. 5B providing a bottom elevation view. Tine housing 512 may be an example of tine housing 312 (FIG. 3, 4). Longitudinal axis L1 may extend through tine housing 512.

Tine housing 512 includes receptor recess 522, receptor recess 524, and receptor recess 525 extending into tine housing 512 from tine housing bottom surface 527. Each of receptor recesses 522, 524, 525 are configured to receive a locking tab such as locking tab 310 comprising mounting structure 308 (FIG. 4), and may comprise a longitudinal portion and a locking portion. As an example, receptor access 522 includes a longitudinal portion 521 extending from tine housing bottom surface 527 and into tine housing 512 in a direction substantially parallel to longitudinal axis L1. Receptor access 522 further includes locking portion 523, which extends from longitudinal portion 521 into tine housing 512 in a direction substantially perpendicular to longitudinal portion 521. Selected portions of receptor access 522 are additionally illustrated with hidden lines in FIG. 5A, indicating a generally L-shaped cross-section when viewed from vantage generally perpendicular to L1. Once a locking tab such as locking tab 310 (FIG. 3) is received within the longitudinal portion 521 of receptor recess 522, tine housing 512 may be rotated around the longitudinal axis L1 to place the locking tab within locking portion 523 of receptor recess 522. Tine housing bottom surface 527 may be configured to contact and/or about elongated housing distal end 306 when tine housing 512 receives a locking tab.

Receptor recess 522 may include a bearing surface 526 configured to substantially trap tine housing 512 against movement (relative to the locking tab) in a direction parallel to longitudinal axis L1. Locking portion 523 may include bearing surface 526. Bearing surface 526 is configured to provide a reaction force against an object—such as some portion of locking tab 310 (FIG. 4)—when the object applies an action force on bearing surface 526 in the proximal direction P. For example, when some portion of locking tab 310 resides within locking portion 523 and applies an action force in the direction F3 on bearing surface 526, bearing surface 526 is configured to provide a reaction force on locking tab 310 in the direction F4. In this manner, when receptor recess 522 receives a locking tab such as locking tab 310 and establishes a configuration where locking tab 310 bears on bearing surface 526, locking tab 310 may substantially secure tine housing 512 against movement (relative to locking tab 310) in a direction parallel to longitudinal axis L1.

Additionally, longitudinal portion 521 of receptor recess may define a portion of inner chamber 316 (FIG. 4) when tine housing 512 is rotated around longitudinal axis L1 to insert locking tab 310 into locking portion 523. FIGS. 5A and 5B further illustrates an adhesive fill port 514 passing through tine housing 512 and into receptor recess 522.

IMD 300 is configured such that receiving one or more locking tabs 310 of mounting structure 308 within tine housing 312 forms inner chamber 316. As discussed, inner chamber 316 is bounded at least some portion of elongated housing distal end 306, mounting structure 308, and tine housing 312. Adhesive fill port 314 is in fluid communication with inner chamber 316, such that an adhesive may be directed into inner chamber 316 through adhesive fill port 314. The adhesive may form a contiguous mass of adhesive which substantially fills inner chamber 316 and contacts elongated housing distal end 306, mounting structure 308, and tine housing 312. The contiguous mass of adhesive may also contact feedthrough pin 318 extending from elongated housing distal end 306 and into tine housing 312. Allowing the contiguous mass of adhesive to solidify provides an arrangement whereby the solidified adhesive serves as a fastening method among the tine housing 312, mounting structure 308, and elongated housing distal end 306. Forming and utilizing inner chamber 316 in this manner may reduce the number of fastening steps between components that might otherwise be necessary. For example, forming and utilizing inner chamber 316 in this manner may reduce the number of individual adhesive applications, individual mechanical fasteners, individual screw threadings, and/or individual snap-fit components between components that might otherwise be necessary.

As discussed, one or more tines comprising the plurality of tines 301 (FIG. 3) may extend distally from tine housing 312 and radially from IMD longitudinal axis L to provide a stabilizing structure to enhance the placement and/or security of electrode 320 against tissue. The plurality of tines 301 may be configured to extend outwardly from tine housing 312 in a substantially symmetric manner around IMD longitudinal axis L (FIG. 3). The shape of one or more tines such as tine 303a and/or 303b may be selected to control deployment, tissue fixation, and/or tissue disengagement. One or more tines comprising the plurality of tines 301 may extend distally from tine housing 312 and radially from IMD longitudinal axis L to provide a stabilizing structure to enhance the placement and/or security of electrode 320 against tissue. Further, one or more tines may be configured assume different configurations depending on forces (or absence thereof) applied to the tines.

For example, when a tine is in a relaxed, substantially zero-stress condition, the tines may be resiliently biased to assume a configuration similar to that depicted by FIG. 3, where tine 303a proceeds from fixed end 332, extends distally from tine housing 312 and radially away from IMD longitudinal axis L, before then extending proximally to a free end 334. In this relaxed condition, free end 334 may be proximal to fixed end 332. In some examples, in the relaxed condition, tine housing 312 and/or plurality of tines 301 is configured such that electrode 320 extends distally beyond the plurality of tines 301. This may allow the plurality of tines 301 to stabilize electrode 320 against tissue in a manner avoiding penetration of the tissue by the tines. For example, tine 303a may define a maximum tine displacement distal to elongated housing distal end 306 and parallel to IMD longitudinal axis L (e.g., at distal-most point 335), and electrode 320 may define a maximum electrode displacement distal to elongated housing distal end 306 and parallel to IMD longitudinal axis L (e.g., at point 335), with the maximum electrode displacement greater than the maximum tine displacement.

The plurality of tines 301 may assume an extended configuration when a structure imparts forces tending to displace the plurality of tines 301 toward longitudinal axis L. For example, inner surface 178 of tubular sidewall 180 may impart forces displacing one or more tines into the extended configuration depicted by the plurality of tines 101 in FIG. 2. In the extended configuration, free end 334 is distal to fixed end 332 (FIG. 3). When the plurality of tines 301 is resiliently biased to assume the relaxed configuration of FIG. 3 in a substantially zero-stress position, the ability to assume the extended configuration of FIG. 2 allows IMD 300 to establish a more radially compact form during delivery to a target site.

Figure 6A:
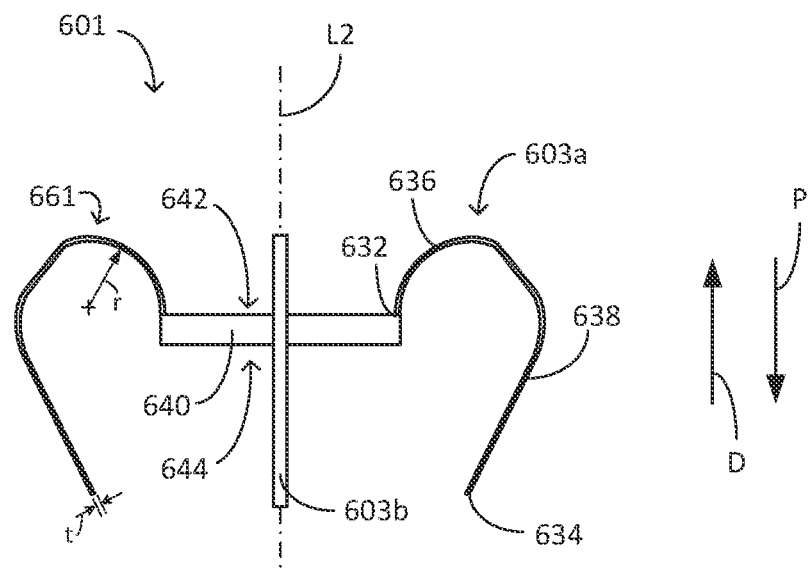
FIG. 6A is a front elevation view illustrating an example plurality of tines.
Figure 6B:
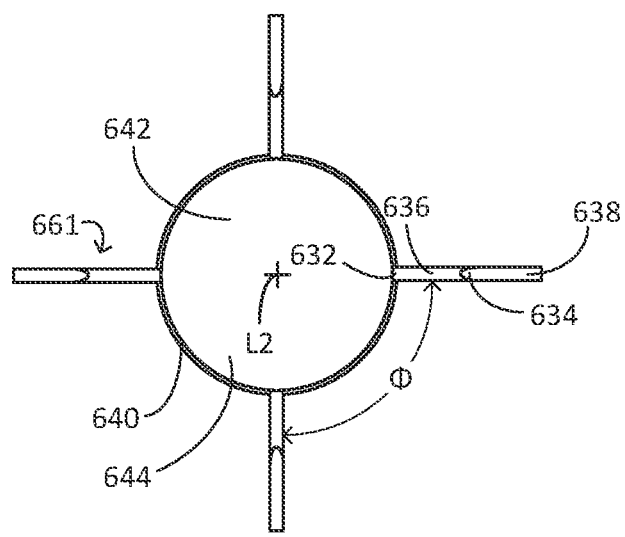
FIG. 6B is a bottom elevation view illustrating the example plurality of tines of FIG. 6A.

As further example, FIG. 6A and FIG. 6B schematically illustrate a plurality of tines 601 including tine 603a and tine 603b. Plurality of tines 601 may be an example of the plurality of tines 301 (FIGS. 3, 4) and plurality of tines 101 (FIG. 1). FIG. 6A provides a front elevation view and FIG. 6B provides a bottom elevation view. For reference, a longitudinal axis L2 extends through the plurality of tines 601. The plurality of tines 601 is depicted in the relaxed configuration. As illustrated, tine 603a includes a first segment 636 which extends distally (direction indicated by D) from fixed end 632 and radially outward from longitudinal axis L2. A second segment 638 extends from first segment 636 to free end 634. In the relaxed condition, free end 634 is proximal (direction indicated by P) to fixed end 632. In examples, and as depicted at FIG. 6A and FIG. 6B, free end 634 is attached to tine ring 640. Each fixed end in the plurality of tines 601 may be attached to tine ring 640. Tine ring 640 may define a first open access 642 and a second open access 644 which substantially surround longitudinal axis L2. First open access 642 and/or second open access may be a substantially circular or oval shape.

Tines within the plurality of tines 601 may be spaced apart relative to one another at any suitable angle Φ, such as an angle within a range from about 60 degrees to 120 degrees, such as 90 degrees. Tine ring 640 may have any suitable inner diameter and outer diameter. In some examples, tine ring 640 may have an inner diameter within a range from about 0.1 inch (2.54 millimeters, mm) to about 0.3 inch (7.62 mm), such as 0.20 inch (5.08 mm), and an outer diameter within a range from about 0.11 inch (2.794 mm) to about 0.31 inch (7.874 mm), such as about 0.21 inch (5.334 mm). In some examples, plurality of tines 610 may be mounted to a tine housing in a manner the same or substantially similar to that described in U.S. Pat. No. 10,099, 050B2, which is incorporated herein by reference in its entirety. In some examples, the plurality of tines 610 may include separately formed tines such as 603*a* that are individually mounted to a tine housing (e.g., not integrated together with tine ring 640).

Tine ring 640 may attach to tine housing 312 (FIG. 3). Tine ring 640 may be configured to attach to tine housing 312 such that, when tine ring 640 attaches to tine housing 312 and longitudinal axis L2 is substantially coincident with or parallel to longitudinal axis L (FIG. 3), the plurality of tines 601 (in the relaxed configuration) extend radially outward from longitudinal axis L and the free end of each tine is proximal to the fixed end of each tine. The free end of each tine may be proximal to tine ring 640.

As discussed, IMD 300 may contain electronic circuitry, including one or more of sensing circuitry (e.g., for sensing cardiac signals), therapy delivery circuitry (e.g., for generating cardiac pacing pulses), and processing circuitry for controlling the functionality of IMD 300. The electronic circuitry may be enclosed by a hermetically sealed chamber (not shown) within elongated housing 302 of IMD 300. Feedthrough pin 318 may establish electrical connectivity between the circuitry and the distal-most electrode 320. Feedthrough pin 318 may include a conductive pin, which is electrically insulated from elongated housing 302 by an insulator, such as glass. Second electrode 321 may function in conjunction with electrode 320 for bipolar pacing and sensing. The electronic circuitry may be configured to generate and deliver an electrical pulse therapy to tissue proximate electrode 320 and through the tissue to second electrode 321.

Feedthrough pin 318 may exit elongated housing 302 as part of a hermetic feedthrough assembly 328 in contact with and/or affixed to elongated housing distal end 306. Hermetic feedthrough assembly 328 may include the feedthrough pin 318, a ferrule 319, and an insulator 317 (such as glass). Ferrule 319 may at least partially surround insulator 317, and insulator 317 may at least partially surround feedthrough pin 318. Insulator 317 may separate feedthrough pin 318 and ferrule 319. Ferrule 319 may be in contact with elongated housing distal end 306. Hermetic feedthrough assembly 328 is configured to maintain a hermetic seal as feedthrough pin 318 extends through elongated housing distal end 306 and through tine housing 312 to establish electrical connectivity with electrode 320. Hermetic feedthrough assembly 328 may be configured to include a gap G between feedthrough pin 318 and ferrule 319 to allow a flow of adhesive to enter the area between feedthrough pin 318 and ferrule 319 when the adhesive fills inner chamber 316. This may positively contribute to the radial and lateral stability provided to feedthrough pin 318 when the adhesive cures into a solidified adhesive structure. The solidified adhesive structure may also contribute to electrical isolation between the feedthrough pin and other components of the IMD, such as ferrule 319, lower tine housing 846, and/or upper tine housing 848. The solidified adhesive structure may provide fluid protection and/or isolation to some portion of or all of hermetic feedthrough assembly 328, such as insulator 317, ferrule 319, and/or the hermetically sealed chamber (not shown) within elongated housing 302. Ferrule 319 may include a tapered structure configured to be in fluid communication with inner chamber 316 to assist the flow of adhesive into gap G.

Tine housing 312 may include a second fill port 313 (FIG. 4). Second fill port 313 may be located distal to fill port 314 (e.g., may be displaced from elongated housing distal end 306 a greater amount than fill port 314). Second fill port 313 is configured to bond MCRD 350 within electrode 320 using adhesive. Electrode 320 may contain corresponding crossholes 322 to dispense the adhesive within the electrode bore via second fill port 313. This may minimize potential contamination of electrode 320 with adhesive. Cross-holes 322 are in fluid communication with some portion of MCRD 350 and electrode 320. Cross-holes 322 may be configured to distribute adhesive to both MCRD 350 and electrode 320, such an adhesive filling cross-holes 322 is in contact with both MCRD 350 and electrode 320.

Figure 7:
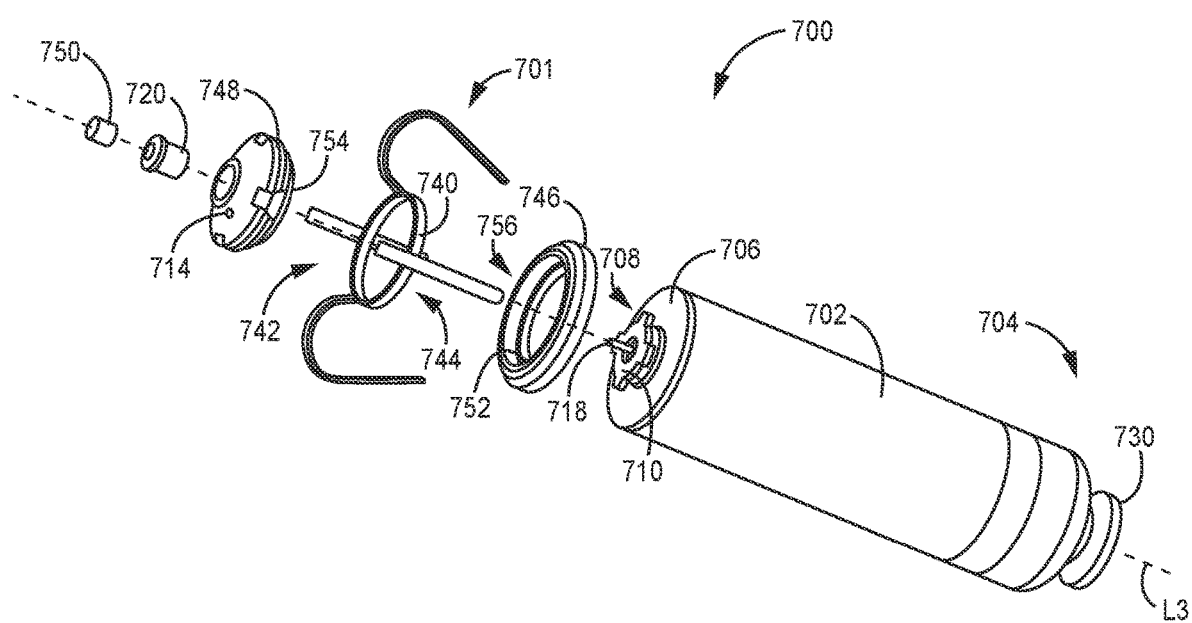
FIG. 7 is an exploded view of an illustrative IMD.

In examples, a tine housing may comprise an upper tine housing and a lower tine housing, and the tine housing may be configured to trap a plurality of tines (e.g., a tine ring) between the upper tine housing and the lower tine housing. The upper tine housing may be configured to receive one or more locking tabs of the mounting structure, and interaction of the locking tabs and the upper tine housing may function to substantially secure both the plurality of tines and the lower tine housing against movement relative to the elongated housing distal end. For example, FIG. 7 depicts an exploded view of an example IMD 700. IMD 700 includes elongated housing 702, elongated housing proximal end 704, elongated housing distal end 706, mounting structure 708, locking tab 710, adhesive fill port 714, feedthrough pin 718, electrode 720, retrieval structure 730, tine ring 740, first open access 742, second open access 744, and MCRD 750, which may be configured similarly to and operate relative to each other in the same manner as the like-named components of IMD 100, IMD 300, tine housing 512, and/or plurality of tines 601.

As depicted by FIG. 7, a mounting structure 708 is attached to elongated housing distal end 706 and includes one or more locking tabs such as locking tab 710. A longitudinal axis L3 extends through elongated housing 702 from elongated housing proximal end 704, elongated housing distal end 706, and mounting structure 708. A tine housing includes lower tine housing 746 and upper tine housing 748. Lower tine housing 746 is configured to contact and/or abut elongated housing distal end 706 and surround mounting structure 708 and longitudinal axis L3. Lower tine housing 746 may be substantially elliptical (e.g. Circular) or oval shaped. Lower tine housing may be configured to provide a clearance around mounting structure 708 when placed in contact with elongated housing distal end 706. Lower tine housing 746 may include an inner shelf 752 around an interior (facing longitudinal axis L3) of lower tine housing 746. The inner shelf may be configured to surround longitudinal axis L3 when lower tine housing 746 contacts and/or abuts elongated housing distal end 706.

A plurality of tines 701 includes a tine ring 740 having a first open access 742 and a second open access 744. A portion of the plurality of tines 701, such as tine ring 740, is configured to insert within lower tine housing 746. The plurality of tines 701 may be configured such that, when lower tine housing 746 contacts and/or abuts elongated housing distal end 706, tine ring 740 may be positioned to contact inner shelf 752 as longitudinal axis L3 intersects both first open access 742 and second open access 744. Some portion of inner shelf 752 may be configured to insert into second open access 744 of tine ring 740. This is illustrated at FIG. 4, where tine ring 340 is positioned on inner shelf 352 of lower tine housing 346 as lower tine housing 746 contacts and/or abuts elongated housing distal end 306, with some portion of inner shelf 352 inserted into the second open access of tine ring 340. Tine ring 740, 340 may be configured to mate with lower tine housing 746, 346 in alternate manners. For example, tine ring 740, 340 may be configured to mate with lower tine housing 746, 346 using a thread connection, a snap-fit, and interference fit, an adhesive, welding, or any other mating and/or affixing techniques.

Upper tine housing 748 is configured to receive locking tab 710 in a receptor recess (not shown). Upper tine housing may include one or more receptor recesses substantially similar in configuration and operation to receptor recess 522, receptor recess 524, and/or receptor recess 525 (FIG. 5A, 5B). Upper tine housing 748 may receive locking tab 710 in substantially the same manner as tine housing 312 receives locking tab 310 (FIG. 3, 4). When upper tine housing 748 receives locking tab 710, locking tab 710 acts to trap upper tine housing 748 to substantially prevent movement of upper tine housing 748 (relative to elongated housing distal end 706) in a direction parallel to longitudinal axis L3. As discussed below, when locking tab 710 traps upper tine housing 748, upper tine housing 748 may correspondingly act to substantially secure plurality of tines 701 and/or lower tine housing 746 against movement (relative to elongated housing distal end 706) in a direction parallel to longitudinal axis L3.

Upper tine housing 748 may be configured to mate with lower tine housing 746 in a manner which positions the plurality of tines 701 between upper tine housing 748 and lower tine housing 746. Upper tine housing may be configured to form a portion of an inner chamber (not shown) with elongated housing distal end 706 and mounting structure 708 when upper tine housing 748 mates with lower tine housing 746. Upper tine housing 748 may comprise an adhesive fill port configured to establish fluid communication with the inner chamber when upper tine housing 748 mates with lower tine housing 746. This is illustrated at FIG. 4, where upper tine housing 348 is mated with lower tine housing 346 in a manner whereby inner chamber 316 is bounded at least in part by upper tine housing 746, elongated housing distal end 306, and mounting structure 308. Adhesive fill port 314 extends through upper tine housing 348 and is in fluid communication with inner chamber 316. Adhesive fill port 314, 714 may be utilized to deliver an adhesive into the inner chamber formed when upper tine housing 348, 748 mates with lower tine housing 346, 746. The adhesive may be administered to form a contiguous mass of adhesive in contact with some portion of tine housing 312, 712 and elongated housing distal end 306, 706, such that curing of the contiguous mass of adhesive affixes tine housing 312, 712 to elongated housing distal end 306, 706 (and vice-versa).

Upper tine housing 748 may be substantially elliptical (e.g., circular) or oval shaped. Upper tine housing 748 may mate with lower tine housing 746 in any manner which positions the plurality of tines 701 between upper tine housing 748 and lower tine housing 746, when the plurality of tines 701 inserts into lower tine housing 746. In examples, upper tine housing 748 or lower tine housing 746 defines a protrusion, and the other of the upper tine housing 748 or lower tine housing 746 defines a recess configured to receive the protrusion. For example, FIG. 7 illustrates recess 756 of lower tine housing 746 configured to receive protrusion 754 of upper tine housing 748. Additionally, at least first open access 742 of plurality of tines 701 may be configured to receive protrusion 754 when upper tine housing 748 traps plurality of tines 701 between upper tine housing 748 and lower tine housing 746. This is illustrated at FIG. 4, where the protrusion of upper tine housing 348 is configured to insert with lower tine housing 346 and the first open access of the plurality of tines 301. Upper tine housing 748, 348 may be configured to mate with lower tine housing 746, 346 and/or the plurality of tines 301, 701 in alternate manners. For example, upper tine housing 748, 348 may be configured to mate with lower tine housing 746, 346 and/or the plurality of tines 301, 701 using a thread connection, a snap-fit, and interference fit, an adhesive, welding, or any other mating and/or affixing techniques. In examples, upper tine housing 748 is configured to surround longitudinal axis L3 when upper tine housing 748 traps the plurality of tines 701 between upper tine housing 748 and lower tine housing 746.

Upper tine housing may be configured such that feedthrough pin 718 extends through the inner chamber (e.g., inner chamber 316, FIG. 3) formed when upper tine housing 748 mates with lower tine housing 746. This is illustrated at FIG. 4, where feedthrough pin 318 extends from elongated housing distal end 306 and through inner chamber 316 when upper tine housing 348 mates with lower tine housing 346. With feedthrough pin 318, 718 extending through the inner chamber (such as inner chamber 316), a contiguous mass of adhesive administered through adhesive fill port 314, 714 may additionally contact some portion of feedthrough pin 318, 718 in addition to tine housing 312, 712 and elongated housing distal end 306, 706. Curing of the contiguous mass of adhesive may provide additional lateral and radial support to feedthrough pin 318, 718 as it extends through the inner chamber (such as inner chamber 316). This may provide advantage when a tine housing is configured such electrode 320, 720 extends distally beyond a maximum distal displacement of the plurality of tines 301, 701 when the plurality of tines 301, 701 is in the relaxed condition, as previously discussed.

As discussed, an IMD may contain electronic circuitry and a feedthrough pin (e.g. feedthrough pin 318) establishing electrical connectivity between the circuitry and the distal-most electrode (e.g., electrode 320, FIG. 4). The feedthrough pin may exit the elongated housing as part of a hermetic feedthrough assembly including a ferrule in contact with and/or affixed to the elongated housing distal end (e.g., elongated housing distal end 306), or may exit the elongated housing as part of an integrated feedthrough assembly where the ferrule is absent. The elongated housing distal end may be configured to accommodate a feedthrough and an insulator in the absence of a ferrule.

Figure 9:
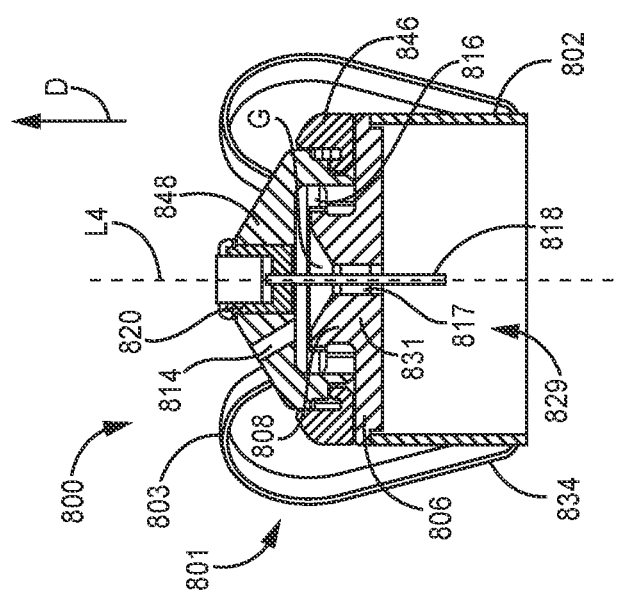
FIG. 9 is a schematic cross-sectional view of the example IMD of FIG. 8.
Figure 8:
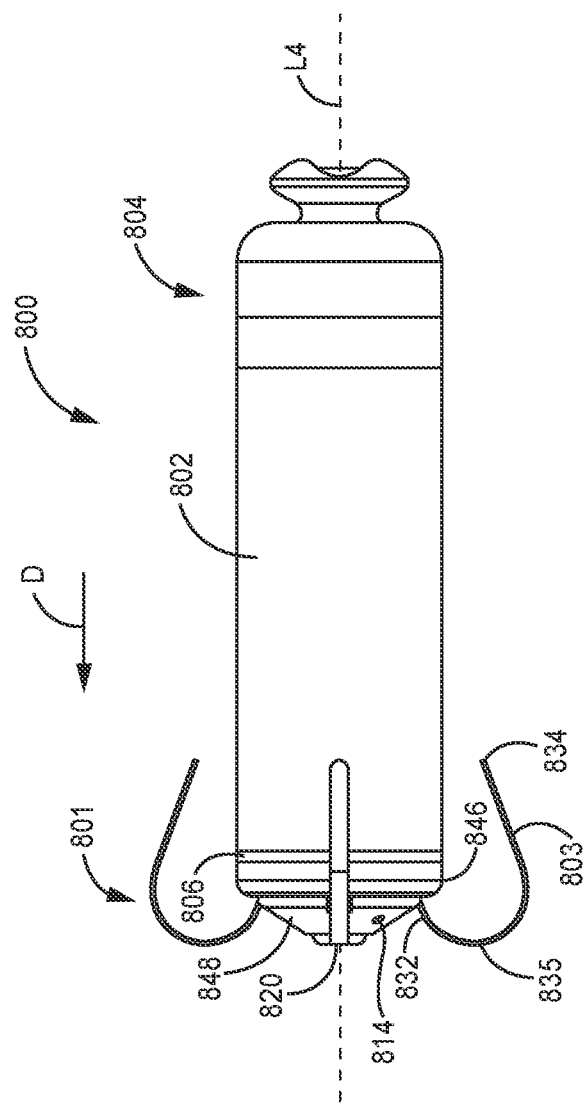
FIG. 8 is an elevation view illustrating another example IMD including a tine housing and elongated housing.

For example, FIG. 8 illustrates an example IMD 800, with FIG. 9 illustrating a cross-section of IMD 800 using a cutting plane perpendicular to longitudinal axis L4. Longitudinal axis L4 extends through elongated housing proximal end 804 and elongated housing distal end 806. IMD 800 may be an example of IMD 100 (FIG. 1), IMD 300 (FIG. 3,4), and/or IMD 700 (FIG. 7). IMD 800 includes elongated housing 802, elongated housing proximal end 804, elongated housing distal end 806, mounting structure 808, adhesive fill port 814, inner chamber 816, feedthrough pin 818, insulator 817, electrode 820, lower tine housing 846, upper tine housing 848, plurality of tines 801, and tine 803 having fixed end 832, free end 834, and distal-most point 835, which may be configured similarly to and operate relative to each other in the same manner as the like-named components of IMD 100, IMD 300, tine housing 512, plurality of tines 601, and/or IMD 700. The distal direction relative to IMD 800 is indicated by D.

IMD 800 includes an integrated feedthrough assembly 829 comprising feedthrough pin 818 and insulator 817. The elongated housing distal end 806 is configured to include a feedthrough section 831. The feedthrough section 831 may be an integral with elongated housing distal end 806. Feedthrough section 831 of elongated housing distal end 806 may at least partially surround insulator 817, and insulator 817 may at least partially surround feedthrough pin 818. Insulator 817 may separate feedthrough pin 818 and feedthrough section 831. The feedthrough section 831 may provide for the gap G into which the adhesive may flow when directed into inner chamber 816 via adhesive fill port 814. Use of the feedthrough section 831 may allow for an increased gap G, and may enhance the flow of adhesive to the area between elongated housing distal end 806 and feedthrough pin 818. The adhesive may form a solidified adhesive structure that may also contribute to electrical isolation between feedthrough pin 818 and other components of the IMD, such as feedthrough section 831, lower tine housing 846, and upper tine housing 848. The solidified adhesive structure may provide fluid protection and/or isolation to some portion of or all of hermetic feedthrough assembly 328, such as insulator 317. IMD 800 may include, rather than the integrated feedthrough assembly 829, a hermetic feedthrough assembly configured similarly to hermetic feedthrough assembly 328 (FIG. 4).

Further, IMD 800 is configured such that a maximum distal displacement (in the direction D) of electrode 820 is less than or equal to maximum distal displacement of tine 803 (e.g., point 835 of tine 803), when tine 803 is in the relaxed condition. This relationship may be beneficial in certain circumstances when IMD 800 is utilized to provide stimulation to particular target sites in a patient. Here and elsewhere, the maximum distal displacement of a component means a maximum distance along a longitudinal axis between a longitudinal axis entry point and a distal displacement point, where the longitudinal axis entry point is the point where the longitudinal axis initially intersects a proximal end of an IMD, and the distal displacement point is a point on the longitudinal axis and co-planer with a plane intersecting the component and perpendicular to the longitudinal axis.

For example, FIG. 10 illustrates an example IMD 1000, with FIG. 11 illustrating a cross-section of IMD 1000 using a cutting plane perpendicular to longitudinal axis L5. Longitudinal axis L5 extends through elongated housing proximal end 1004 and elongated housing distal end 1006. IMD 1000 may be an example of IMD 100 (FIG. 1), IMD 300 (FIG. 3,4), IMD 700 (FIG. 7), and/or IMD 800 (FIG. 8, 9). IMD 1000 includes elongated housing 1002, elongated housing proximal end 1004, elongated housing distal end 1006, mounting structure 1008, adhesive fill port 1014, second fill port 1113, inner chamber 1016, electrode 1020, hermetic feedthrough assembly 1028 including feedthrough pin 1018, lower tine housing 1046, upper tine housing 1048, plurality of tines 1001, and tine 1003 having fixed end 1032, free end 1034, and distal-most point 1035, which may be configured similarly to and operate relative to each other in the same manner as the like-named components of IMD 100, IMD 300, tine housing 512, plurality of tines 601, IMD 700, and/or IMD 800. The distal direction relative to IMD 1000 is indicated by D. IMD 1000 may include, rather than the hermetic feedthrough assembly 1028, an integrated feedthrough assembly configured similarly to integrated feedthrough assembly 829 (FIG. 8).

FIG. 10 illustrates longitudinal axis L5 initially intersecting IMD 1000 at a point P1. The maximum distal displacement of tine 1003 is defined by a maximum distance from point P1 to a geometric plane which is both perpendicular to longitudinal axis L5 and which includes some part of tine 103. At FIG. 10, this is represented by distal-most point 1035, where a geometric plane (represented by E1, showing the edge of the geometric plane) includes a portion of tine 1003 and is perpendicular to longitudinal axis L5. The distance D1 is the maximum distance from point P1 to the intersection point of a plane perpendicular to longitudinal axis L5 which also includes some portion of tine 1003. In similar fashion, the maximum distal displacement of electrode 1020 is defined by a maximum distance from point P1 to a geometric plane which is both perpendicular to longitudinal axis L5 and which includes some part of electrode 1020. At FIG. 10, this is represented by distal-most point P2, where a geometric plane (represented by E2, showing the edge of the geometric plane) includes a portion of electrode 1020 and is perpendicular to longitudinal axis L5. The distance D2 is the maximum distance from point P1 to the intersection point of a plane perpendicular to longitudinal axis L5 which also includes some portion of electrode 1020. Within the IMDs disclosed, the maximum distal displacement of an electrode (such as electrode 320, 820, 1020, and/or 1220 discussed below) may be greater than, equal to, or less than a maximum distal displacement of one or more tines in a plurality of tines (such as plurality of tines 101, 301, 601, 701, 801, 1001, and/or 1201 discussed below.) In some examples, a distance between the maximum distal displacement of an electrode (e.g., electrode 320, 820, 1020, and/or 1220) and the maximum distal displacement of one or more tines in a plurality of tines (such as plurality of tines 101, 301, 601, 701, 801, 1001, and/or 1201) is approximately 2 millimeters (mm). For example, the distance between the maximum distal displacement of the electrode and the maximum distal displacement of the one or more tines may be between 1 mm and 3 mm.

Figure 13:
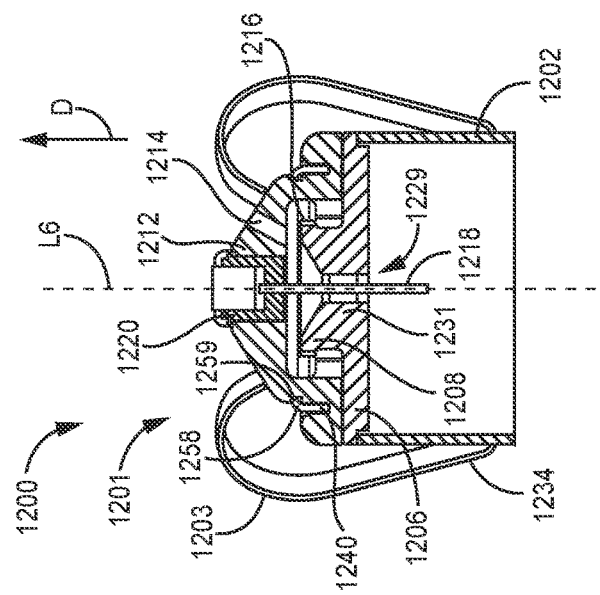
FIG. 13 is a schematic cross-sectional view of the example IMD of FIG. 12.
Figure 12:
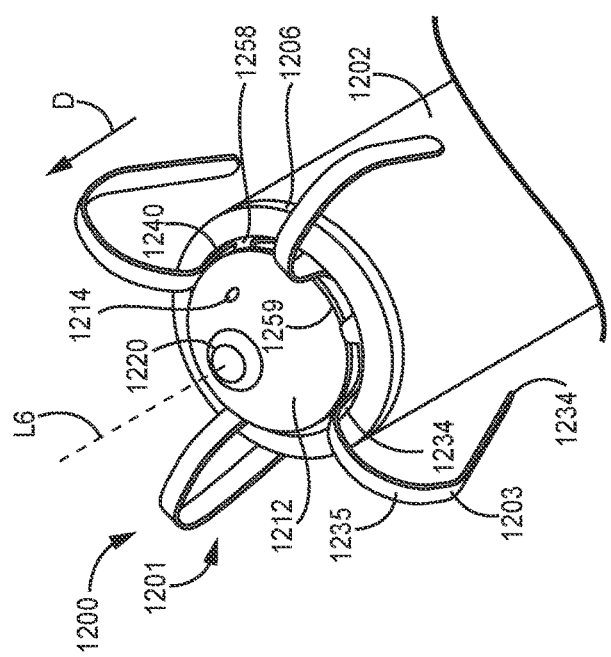
FIG. 12 is a perspective view illustrating a further example IMD including a tine housing and elongated housing.

As discussed, a plurality of tines may be configured to mate with a tine housing using a thread connection, a snap-fit, and interference fit, an adhesive, welding, or any other mating and/or affixing techniques. As an example, FIG. 12 illustrates an example IMD 1200, with FIG. 13 illustrating a cross-section of IMD 1200 using a cutting plane perpendicular to longitudinal axis L6. Longitudinal axis L6 extends through a proximal end (not shown) of elongated housing 1204 and elongated housing distal end 1206. IMD 1200 may be an example of IMD 100 (FIG. 1), IMD 300 (FIG. 3,4), IMD 700 (FIG. 7), IMD 800 (FIG. 8, 9), and/or IMD 1000 (FIG. 10, 11). IMD 1200 includes elongated housing 1202, elongated housing distal end 1206 including feedthrough section 1231, mounting structure 1208, adhesive fill port 1214, inner chamber 1216, electrode 1220, integrated feedthrough assembly 1229 including feedthrough pin 1218, tine housing 1212, plurality of tines 1201, tine ring 1240, and tine 1203 having fixed end 1232, free end 1234, and distal-most point 1235, which may be configured similarly to and operate relative to each other in the same manner as the like-named components of IMD 100, IMD 300, tine housing 512, plurality of tines 601, IMD 700, IMD 800, and/or IMD 1000. The distal direction relative to IMD 1200 is indicated by D. IMD 1200 may include, rather than the integrated feedthrough assembly 1229, a hermetic feedthrough assembly configured similarly to hermetic feedthrough assembly 328, 828 (FIG. 4, FIG. 9).

Tine housing 1212 of IMD 1200 is configured to secure the plurality of tines using a snap-fit with one or more tabs 1258 of tine ring 1240. Tine housing 1212 may define a recess 1259 configured to receive the one or more tabs 1258. Recess 1259 may be a discrete recess configured to receive a single tab of tine ring 1240, or recess 1259 may be configured to receive a plurality of tabs of tine ring 1240. When the one or more tabs 1258 insert into recess 1259 of tine housing 1212, tine housing 1212 secures tine ring 1240 to substantially prevent motion of tine ring 1240 relative to tine housing 1212.

Figure 14:
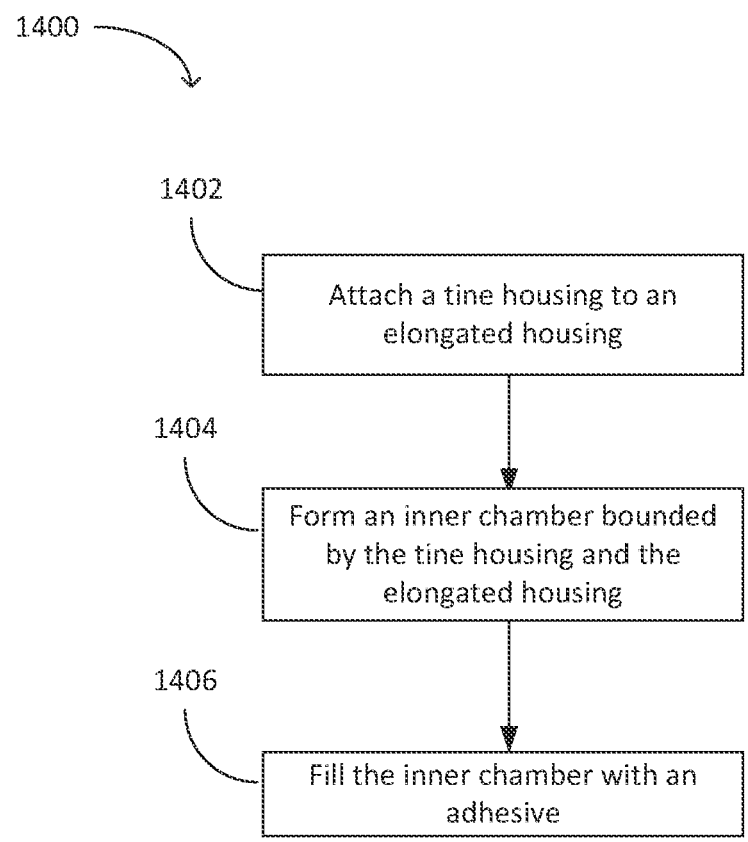
FIG. 14 illustrates an example technique for assembling an example IMD.

FIG. 14 illustrates a flow diagram of an example technique 1400 assembling a medical device. Although the technique is described with various reference to IMD 100 (FIG. 1, 2), IMD 300 (FIG. 3, 4), IMD 700 (FIG. 7), IMD 800 (FIG. 8, 9), IMD 1000 (FIG. 10, 11), and IMD 1200 (FIG. 12, 13), in other examples, the technique may be used with another medical device.

The technique includes attaching at least some portion of a tine housing 312 (FIG. 3, 4) to an elongated housing 302 of the medical device by receiving at least one locking tab 310 of a mounting structure 308 in the portion of tine housing 312 (1402). Mounting structure 308 may be attached to an elongated housing distal end 306. Receiving the locking tab may include receiving locking tab 310 in a receptor recess of the portion of tine housing 312, such as receptor recess 522 (FIG. 5A, 5B). The technique may include receiving locking tab 310 in a longitudinal portion 521 of receptor recess 522, and rotating the portion of tine housing 312 around a longitudinal axis L in order to insert locking tab into a locking portion 523 of receptor recess 522, wherein the longitudinal axis L extends from elongated housing proximal end 304 to elongated housing distal end 306. Inserting locking tab 310 into locking portion 523 may include contacting locking tab 310 and a bearing surface 526 of receptor recess 522 to substantially secure some portion of tine housing 312 against movement relative to elongated housing 302 and parallel to the longitudinal axis L.

The technique includes forming an inner chamber 316 when tine housing 312 receives locking tab 310 (1404). Forming inner chamber 316 may include bounding inner chamber 316 at least in part with some portion of tine housing 312, mounting structure 308, and elongated housing distal end 306. The technique may include rotating tine housing 312 about longitudinal axis L and establishing the longitudinal portion 521 of receptor recess 522 within inner chamber 316.

The technique includes filling inner chamber 316 of the medical device with an adhesive using adhesive fill port 314 in fluid communication with inner chamber 316, where tine housing 312, mounting structure 308, and elongated housing distal end 306 form some portion of the boundary of inner chamber 316 (1406). The technique may include forming inner chamber 316 by receiving locking tab 310 in receptor recess 522 (FIG. 5A, 5B). Forming inner chamber 316 may include rotating tine housing 312 around the longitudinal axis L to include longitudinal portion 521 of receptor recess 522 within inner chamber 316. The technique may include venting inner chamber 316 through vent port 315 while filling inner 316 with adhesive through adhesive fill port 314 (FIG. 3). The technique may include forming a contiguous mass of the adhesive in inner chamber 316 and contacting the contiguous mass of the adhesive with the elongated housing distal end 306, mounting structure 308, and tine housing 312. In some examples, filling inner chamber 316 with the adhesive comprises pouring the adhesive into adhesive fill port 314 as a liquid, and allowing the adhesive to cure into a solid within inner chamber 316.

The technique may include inserting feedthrough pin 318 through tine housing 312, through inner chamber 316, and into elongated housing 302 prior to pouring the adhesive into adhesive fill port 314. The technique may include contacting the feedthrough pin with the contiguous mass of the adhesive in inner chamber 316.

In some examples, the technique includes surrounding longitudinal axis L with a tine ring 340, wherein one or more tines such as 3030a and/or 303b extend from tine ring 340, and then trapping tine ring 340 using tine housing 312, to substantially prevent motion of tine ring 340 relative to tine housing 312. Trapping the tine ring using the tine housing may include inserting a tab 1258 of tine ring 1240 into a recess 1259 of tine housing 1212 (FIG. 12, 13).

In examples, the technique includes assembling tine housing 312 using an upper tine housing 348 and a lower tine housing 346. Assembling the tine housing may include receiving locking tab 310 in a portion of upper tine housing 348, and contacting and/or trapping lower tine housing 346 against the elongated housing distal end 306 when upper tine housing 348 receives the locking tab 310. Receiving the locking tab 310 may include receiving locking tab 310 in a receptor recess of upper tine housing 348, such as receptor recess 522 (FIG. 5A, 5B). The technique may include receiving locking tab 310 in a longitudinal portion 521 of receptor recess 522, and rotating upper tine housing 348 around the longitudinal axis L, in order to insert locking tab 310 into locking portion 523 of receptor recess 522.

The technique may include positioning lower tine housing 346 to contact and/or abut elongated housing distal end 306 prior to receiving locking tab 310 in upper tine housing 348. Positioning lower tine housing 346 may include surrounding some portion of mounting structure 308 and longitudinal axis L. In some examples, contacting and/or trapping lower tine housing 346 against elongated housing distal end 306 using upper tine housing 348 may include trapping a tine ring 340 between upper tine housing 348 and lower tine housing 346, in order to substantially prevent motion of tine ring 340 parallel to longitudinal axis L. Trapping tine ring 340 may include positioning tine ring 340 such that one or more tines such as 303a and/or 303b extend distally from a fixed end such as fixed end 332 and radially away from longitudinal axis L.

The adhesive utilized to fill inner chamber 316 through adhesive fill port 314 may be any substance which may be applied to two or more surfaces and which binds the surfaces together to resist separation and/or movement of the surfaces relative to each other. The adhesive may hold the surfaces together via a chemical bond between the adhesive and the surfaces, electrostatic forces, van der Waals forces, and/or other mechanisms. The adhesive may exist as a liquid under a first thermodynamic, chemical, solvent concentration, or other condition, and exists as a solid under a second thermodynamic, chemical, solvent concentration, or other condition. The adhesive may be a reactive or non-reactive adhesive. The liquid adhesive may comprise single monomers and oligomers which react to form a tridimensional polymeric network when cured into a solid. The adhesive may cure into a solid using heat, radiation, pressure, a catalyst, and/or a curing agent. The curing may be induced by chemical additives or may occur in the absence of additives. Here, curing of an adhesive may refer to a substantial loss of solubility and viscosity of the adhesive.

The plurality of tines 301, 601, 701, 801, 1001, and/or 1201 may include any suitable elastically deformable biocompatible material. In some examples, the plurality of tines may include a super-elastic material, such as, for example, a nickel-titanium alloy. For example, the plurality of tines may be cut from a medical grade nickel-titanium alloy tubing that conforms to the chemical, physical, mechanical, and metallurgical requirements of the ASTM F3063 standard, and has a wall thickness of about 0.005 inch (0.127 mm). One or more tines such as 303a and/or 303b may be integrally formed with tine ring 340, and may have a constant thickness t (FIG. 6) of about 0.005 inch±0.001 inch (0.127 mm±0.0254 mm). In some examples, the one or more tines may be shaped into a preset configuration by bending and holding the one or more tines while heat treating. Heat treating the one or more tines may cause a microstructure of the material of the one or more tines to assume a configuration such that a resting state of the one or more tines (e.g., without application of an external force) is the relaxed configuration. The one or more tines may include a curved section 661 (FIG. 6) having a deformable preset curvature. In some examples, curved section 661 may include a single radius r within a range from about 0.06 inch (1.520B mm) to about 0.08 inch (2.032 mm), such as about 0.067 inch±0.010 inch (1.7018 mm±0.254 mm). In some examples, curved section 661 may include more than one curved section. Free end 334, 634, 834, 1034, and/or 1234 may include any suitable shape, such as, for example, a rounded shape or an incisive shape. The plurality of tines 301, 601, 701, 801, 1001, and/or 1201 may be manufactured using any suitable technique. In some examples, forming the plurality of tines includes forming one or more cutouts, engravings, embossing, or other variations having a constant or a varied thickness t (FIG. 6). For example, cutouts, engravings, embossing, or other variations in the thickness t may be formed by laser etching or chemical etching.

The present disclosure includes the following examples.

Example 1

An implantable medical device comprising: an elongated housing defining a longitudinal axis, wherein the longitudinal axis extends from a proximal end of the elongated housing to a distal end of the elongated housing; a mounting structure attached to the distal end of the elongated housing, wherein the mounting structure comprises one or more locking tabs around the longitudinal axis; a tine housing at least partially surrounding the mounting structure, the tine housing comprising an adhesive fill port and one or more tines extending from the tine housing, and the tine housing configured to receive the one or more locking tabs, wherein the one or more locking tabs are configured to limit motion of the tine housing parallel to the longitudinal axis when the tine housing receives the one or more locking tabs, wherein the tine housing and the mounting structure form an inner chamber bounded at least in part by the distal end of the elongated housing, the mounting structure, and the tine housing when the tine housing receives the one or more locking tabs, and wherein the adhesive fill port is in fluid communication with the inner chamber when the tine housing receives the one or more locking tabs.

Example 2

The implantable medical device of example 1, further comprising a feedthrough pin extending into the elongated housing, wherein the feedthrough pin extends through the tine housing, the inner chamber, and the mounting structure in a direction parallel to the longitudinal axis.

Example 3

The implantable medical device of example 2, further comprising an electrode, wherein the feedthrough pin is electrically coupled to the electrode and electrically coupled to circuitry within the elongated housing.

Example 4

The implantable medical device of example 2 or 3, further comprising an adhesive within the inner chamber.

Example 5

The implantable medical device of any of examples 2-4, further comprising an electrode, wherein the feedthrough pin is electrically coupled to the electrode and electrically coupled to circuitry within the elongated housing.

Example 5

The implantable medical device of example 4, wherein the adhesive is a contiguous mass in contact with the distal end of the elongated housing, the mounting structure, the tine housing, and the feedthrough pin.

Example 6

The implantable medical device of any of examples 1-5, wherein the tine housing comprises an upper tine housing and a lower tine housing, wherein the lower tine housing is attached to the distal end of the elongated housing, and wherein the upper tine housing is configured to receive the one or more tabs, and wherein the upper tine housing is configured to limit motion of the lower tine housing parallel to the longitudinal axis when the upper tine housing receives the one or more locking tabs.

Example 7

The implantable medical device of any of examples 1-6, wherein the tine housing comprises a vent port, and wherein the vent port is in fluid communication with the inner chamber when the tine housing receives the one or more locking tabs.

Example 8

The implantable medical device of any of examples 1-7, wherein at least one tine in the one or more tines define a displacement in the direction parallel to the longitudinal axis and in a direction perpendicular to the longitudinal axis.

Example 9

The implantable medical device of example 8, wherein the one or more tines are attached to a tine ring, wherein the tine ring surrounds the longitudinal axis, and wherein the tine housing is configured to limit motion of the tine ring parallel to the longitudinal axis.

Example 10

The implantable medical device of any of examples 1-9, further comprising an electrode in contact with the tine housing, wherein: the one or more tines define a maximum tine displacement from the distal end of the elongated housing in the direction parallel to the longitudinal axis; the electrode defines a maximum electrode displacement from the distal end of the elongated housing in the direction parallel to the longitudinal axis; and the maximum electrode displacement is greater than the maximum tine displacement.

Example 11

The implantable medical device of example 10, wherein a distance between the maximum electrode displacement and the maximum tine displacement is approximately 2 millimeters.

Example 12

The implantable medical device of any of examples 1-11, wherein the tine housing is configured to receive a locking tab of the one or more locking tabs in at least one tine access, and wherein the tine access comprises a bearing surface configured to provide a reaction force on the locking tab in a direction substantially parallel to the longitudinal axis when the locking tab exerts an action force on the bearing surface in a direction opposite the direction substantially parallel to the longitudinal axis.

Example 13

A method of assembling an implantable medical device comprising: attaching a tine housing of the implantable medical device to an elongated housing of the medical device, wherein the elongated housing defines a longitudinal axis that extends from a proximal end of the elongated housing to a distal end of the elongated housing, and wherein attaching the tine housing to the elongated housing comprises receiving, by the tine housing, at least one locking tab of a mounting structure attached to the distal end of the elongated housing, wherein the at least one locking tab is configured to substantially prevent motion of the tine housing parallel to the longitudinal axis when the tine housing receives the one or more locking tab; and filling an inner chamber of a medical device with an adhesive using an adhesive fill port defined by the tine housing, wherein the tine housing and the mounting structure form the inner chamber bounded at least in part by the distal end of the elongated housing, the mounting structure, and the tine housing when the tine housing receives the one or more locking tabs, and wherein the adhesive fill port is in fluid communication with the inner chamber when the tine housing receives the one or more locking tabs.

Example 14

The method of example 13, wherein the tine housing comprises a vent port in fluid communication with the inner chamber when the tine housing receives the one or more locking tabs, and further comprising venting the inner chamber while filling the inner chamber with the adhesive.

Example 15

The method of example 13 or 14, further comprising forming a contiguous mass of the adhesive in the inner chamber and contacting the contiguous mass of the adhesive and the distal end of the elongated housing, the mounting structure, and the tine housing.

Example 16

The method of example 15, further comprising contacting the contiguous mass of the adhesive with a feedthrough pin extending through the tine housing, through the inner chamber, and into the elongated housing.

Example 17

The method of any of examples 13-16, further comprising assembling the tine housing by: receiving one or more locking tabs in an upper tine housing; and positioning a lower tine housing between the distal end of the elongated housing and the upper tine housing when the upper tine housing receives the one or more locking tabs.

Example 18

The method of example 17, further comprising placing a tine ring between the upper tine housing and the lower tine housing to substantially prevent motion of the tine ring parallel to the longitudinal axis, wherein one or more tines extend from the tine ring.

Example 19

The method of any of examples 13-18, further comprising: surrounding the longitudinal axis with a tine ring, wherein one or more tines extend from the tine ring; and limiting motion of the tine ring parallel to the longitudinal axis when the tine housing receives the one or more locking tabs, wherein the one or more tines extend from the tine housing when the tine housing receives the one or more locking tabs.

Example 20

The method of any of examples 13-19, wherein filling the inner chamber of the medical device with the adhesive comprises: pouring the adhesive into the adhesive fill port as a liquid; and allowing the adhesive to cure into a solid within the inner chamber of the medical device.

Example 21

The method of example 20, further comprising inserting a feedthrough pin through the tine housing, through the inner chamber, and into the elongated housing prior to pouring the adhesive into the adhesive fill port Various examples of the disclosure have been described. Any combination of the described systems, operations, or functions is contemplated. These and other examples are within the scope of the following claims.

What is claimed is:
1. An implantable medical device comprising:
an elongated housing defining a longitudinal axis, wherein the longitudinal axis extends from a proximal end of the elongated housing to a distal end of the elongated housing;
a mounting structure attached to the distal end of the elongated housing, wherein the mounting structure comprises one or more locking tabs around the longitudinal axis;

a tine housing at least partially surrounding the mounting structure, the tine housing comprising an adhesive fill port and one or more tines extending from the tine housing, and the tine housing configured to receive the one or more locking tabs, wherein the one or more locking tabs are configured to limit motion of the tine housing parallel to the longitudinal axis when the tine housing receives the one or more locking tabs, wherein the tine housing and the mounting structure form an inner chamber bounded at least in part by the distal end of the elongated housing, the mounting structure, and the tine housing when the tine housing receives the one or more locking tabs, and wherein the adhesive fill port extends through the tine housing and opens into an open space defined by the inner chamber when the tine housing receives the one or more locking tabs, the open space extending from the mounting structure to a portion of the tine housing and the open space further extending to the distal end of the elongated housing;

an electrode supported by the tine housing and positioned outside of the inner chamber;

a feedthrough pin extending from the distal end of the elongated housing, through the portion of the tine housing, and through the open space, wherein the mounting structure at least partially surrounds the feedthrough pin, and wherein the feedthrough pin is electrically connected to the electrode; and an adhesive filling the open space, wherein the adhesive defines a contiguous mass in contact with the distal end of the elongated housing, the mounting structure, the tine housing, and the feedthrough pin.

2. The implantable medical device of claim 1, wherein the feedthrough pin extends through the inner chamber in a direction parallel to the longitudinal axis.

3. The implantable medical device of claim 2, wherein the feedthrough pin is electrically coupled to circuitry within the elongated housing.

4. The implantable medical device of claim 1, wherein the tine housing comprises an upper tine housing and a lower tine housing, wherein the lower tine housing is attached to the distal end of the elongated housing, and wherein the upper tine housing is configured to receive the one or more locking tabs, and wherein the upper tine housing is configured to limit motion of the lower tine housing parallel to the longitudinal axis when the upper tine housing receives the one or more locking tabs.

5. The implantable medical device of claim 1, wherein the tine housing comprises a vent port, and wherein the vent port is in fluid communication with the inner chamber when the tine housing receives the one or more locking tabs.

6. The implantable medical device of claim 1, wherein at least one tine in the one or more tines define a displacement in a direction substantially parallel to the longitudinal axis and in a direction substantially perpendicular to the longitudinal axis.

7. The implantable medical device of claim 6, wherein the one or more tines are attached to a tine ring, wherein the tine ring surrounds the longitudinal axis, and wherein the tine housing is configured to limit motion of the tine ring parallel to the longitudinal axis.

8. The implantable medical device of claim 1, wherein:
the one or more tines define a maximum tine displacement from the distal end of the elongated housing in a direction parallel to the longitudinal axis;

the electrode defines a maximum electrode displacement from the distal end of the elongated housing in the direction parallel to the longitudinal axis; and the maximum electrode displacement is greater than the maximum tine displacement.

9. The implantable medical device of claim 8, wherein a distance between the maximum electrode displacement and the maximum tine displacement is approximately 2 millimeters.

10. The implantable medical device of claim 1, wherein the tine housing is configured to receive a locking tab of the one or more locking tabs in at least one tine access, and wherein the tine access comprises a bearing surface configured to provide a reaction force on the locking tab in a direction substantially parallel to the longitudinal axis when the locking tab exerts an action force on the bearing surface in a direction opposite the direction substantially parallel to the longitudinal axis.

11. The implantable medical device of claim 1,
wherein the tine housing defines a receptor recess including a longitudinal portion extending from a tine housing bottom surface into the tine housing and a locking portion extending from the longitudinal portion into the tube housing, such that the receptor recess substantially defines an L-shape within a cross-section of the tine housing, wherein the at least one locking tab of the one or more locking tabs is configured to insert into the longitudinal portion when the tine housing receives the one or more locking tabs, wherein the at least one locking tab is configured to insert within the locking portion when the at least one locking tab is inserted within the longitudinal portion and the tine housing is rotated about the longitudinal axis relative to the mounting structure, wherein the locking portion is configured to limit motion of the tine housing parallel to the longitudinal axis when the at least one locking tab is inserted within the locking portion, wherein the longitudinal portion defines a portion of the inner chamber when the at least one locking tab is inserted within the locking portion, and wherein the contiguous mass of adhesive is in contact with the longitudinal portion.

12. A method of assembling an implantable medical device comprising:

receiving, by a tine housing of the implantable medical device, one or more locking tabs of a mounting structure attached to a distal end of an elongated housing of the medical device, wherein the elongated housing defines a longitudinal axis that extends from a proximal end of the elongated housing to a distal end of the elongated housing, and wherein the one or more locking tabs are configured to substantially prevent motion of the tine housing parallel to the longitudinal axis when the tine housing receives the one or more locking tabs;

extending a feedthrough pin through a portion of the tine housing, wherein the feedthrough pin extends from the distal end of the elongated housing, and wherein the feedthrough pin is at least partially surrounded by the mounting structure;

defining, when the tine housing receives the one or more locking tabs, an inner chamber bounded at least in part by the distal end of the elongated housing, the mounting structure, and the tine housing, wherein the inner chamber defines an open space extending from the mounting structure to the portion of the tine housing, the open space further extending to the distal end of the elongated housing, and the feedthrough pin extending through the open space;

electrically connecting the feedthrough pin and an electrode supported by the tine housing and positioned outside of the inner chamber;

filling the open space with an adhesive using an adhesive fill port defined by the tine housing, wherein the adhesive fill port extends through the tine housing and opens into the open space when the tine housing receives the one or more locking tabs, wherein the adhesive defines a contiguous mass within the open space, and wherein the contiguous mass is in contact with the distal end of the elongated housing, the mounting structure, the tine housing, and the feedthrough pin.

13. The method of claim 12, further comprising filling the longitudinal portion when the adhesive fills the open space.

14. The method of claim 12, wherein the tine housing comprises a vent port in fluid communication with the open space when the tine housing receives the one or more locking tabs, and further comprising venting, using the vent port, the inner chamber while filling the open space with the adhesive.

15. The method of claim 12, further comprising assembling the tine housing by:
receiving the one or more locking tabs in an upper tine housing; and
positioning a lower tine housing between the distal end of the elongated housing and the upper tine housing when the upper tine housing receives the one or more locking tabs.

16. The method of claim 15, further comprising placing a tine ring between the upper tine housing and the lower tine housing to substantially prevent motion of the tine ring parallel to the longitudinal axis, wherein one or more tines extend from the tine ring.

17. The method of claim 12, further comprising:
surrounding the longitudinal axis with a tine ring, wherein one or more tines extend from the tine ring; and
limiting motion of the tine ring parallel to the longitudinal axis when the tine housing receives the one or more locking tabs, wherein the one or more tines extend from the tine housing when the tine housing receives the one or more locking tabs.

18. The method of claim 12, wherein filling the inner chamber of the medical device with the adhesive comprises:
pouring the adhesive into the adhesive fill port as a liquid; and
allowing the adhesive to cure into a solid within the inner chamber of the medical device.

19. The method of claim 12, wherein attaching the tine housing to the mounting structure comprises:
receiving at least one locking tab in a longitudinal portion of a receptor recess of the tine housing;
receiving, once the at least one locking tab is received in the longitudinal portion, the at least one locking tab in a locking portion of the receptor recess to limit motion of the tine housing parallel to the longitudinal axis, wherein the longitudinal portion defines a portion of the inner chamber when the tine housing attaches to the mounting structure.

20. The implantable medical device of claim 11, wherein the adhesive fill port opens into the longitudinal portion when the at least one locking tab is inserted within the locking portion.

* * * * *